United States Patent [19]
Saito et al.

[11] Patent Number: 5,119,829
[45] Date of Patent: Jun. 9, 1992

[54] SYSTEM FOR COLLECTING INFORMATION ON HEALTH

[75] Inventors: Shiro Saito; Ryuichi Kawamoto; Mineharu Kondo; Shigeru Sakakibara, all of Aichi, Japan

[73] Assignee: Inax Corporation, Aichi, Japan

[21] Appl. No.: 610,278

[22] Filed: Nov. 7, 1990

Related U.S. Application Data

[62] Division of Ser. No. 195,557, May 18, 1988, Pat. No. 4,982,741.

[30] Foreign Application Priority Data

May 22, 1987 [JP] Japan .................. 62-126447
May 22, 1987 [JP] Japan .................. 62-126448

[51] Int. Cl.⁵ .............................................. A61B 5/00
[52] U.S. Cl. ....................................................... 128/771
[58] Field of Search ............... 128/632, 633, 760, 771, 128/904

[56] References Cited

U.S. PATENT DOCUMENTS

| | | | |
|---|---|---|---|
| 4,216,462 | 8/1980 | McGrath et al. | 128/904 |
| 4,554,687 | 11/1985 | Carter et al. | 128/760 |
| 4,589,280 | 5/1986 | Carter | 128/760 |
| 4,608,996 | 9/1986 | Brown | 128/760 |

*Primary Examiner*—Max Hindenburg
*Attorney, Agent, or Firm*—Kanesaka and Takeuchi

[57] ABSTRACT

An apparatus for examining urine for certain constituents thereof includes a vertically disposed cylinder for receiving urine therein. The cylinder includes a diametrically enlarged upper portion having an inside diameter which is larger than that of its remaining portion. A piston is vertically movably disposed in the cylinder. If the piston is lowered, urine can be stored in the cylinder. If it is raised, the urine is discharged from the cylinder, except that only a small portion thereof remains in a clearance defined between the piston and the diametrically enlarged portion of the cylinder. If the piston is lowered again, a reagent and water are supplied into the cylinder and mixed with the urine remaining therein. An electrode is connected to the cylinder for determining the concentration of sugar, etc. in the urine which has been mixed with the reagent and water. Disclosed also is a toilet stool having a bowl surface in which the upper end of the apparatus is exposed for receiving urine into the cylinder. The toilet stool including the apparatus can be employed to organize a system for collecting information on health. The system includes a first computer provided near the toilet stool for collecting data, such as the concentration of sugar in the urine, and transferring them, and a second computer which may be installed in a hospital for receiving the data from the first computer and storing them progressively.

4 Claims, 25 Drawing Sheets

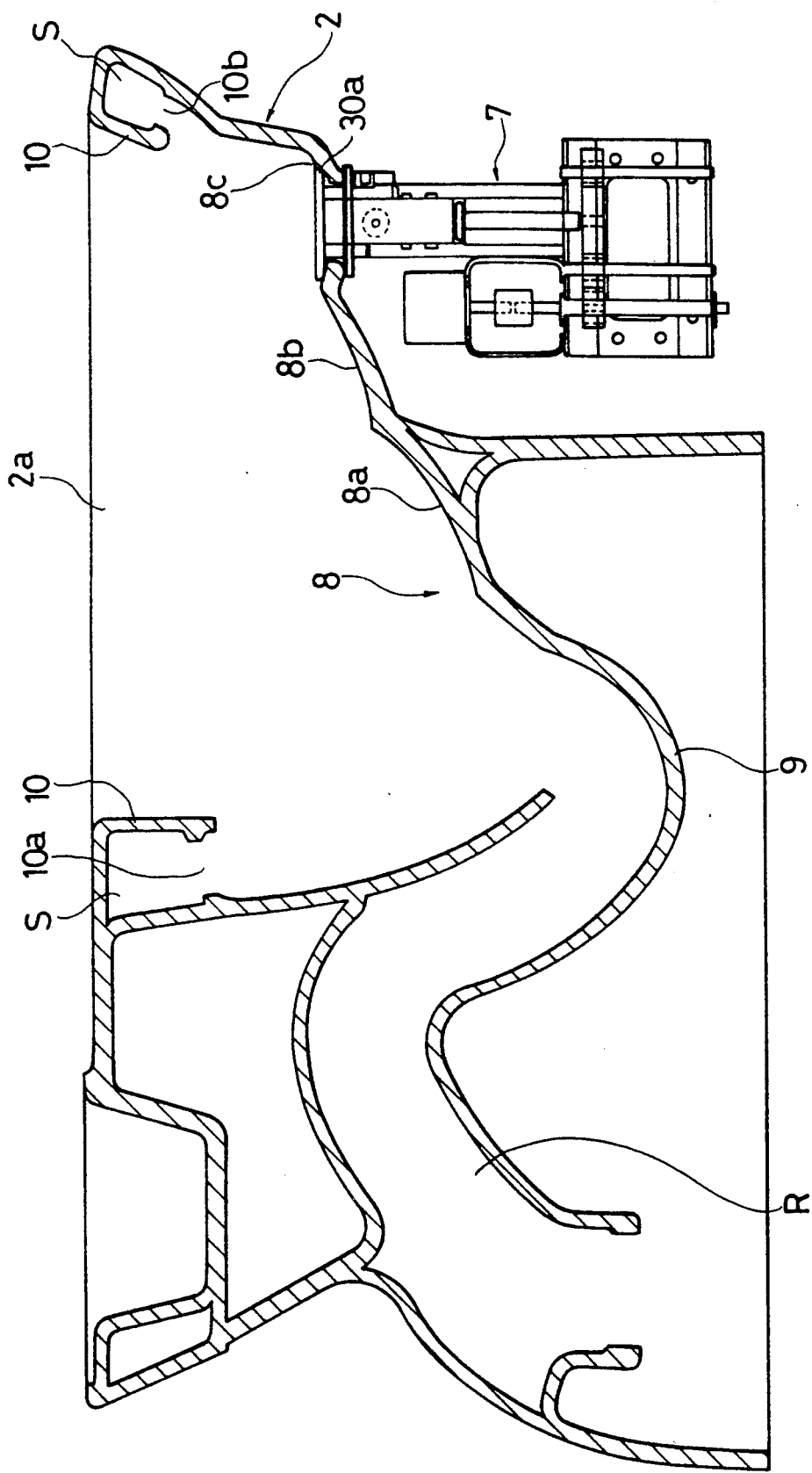

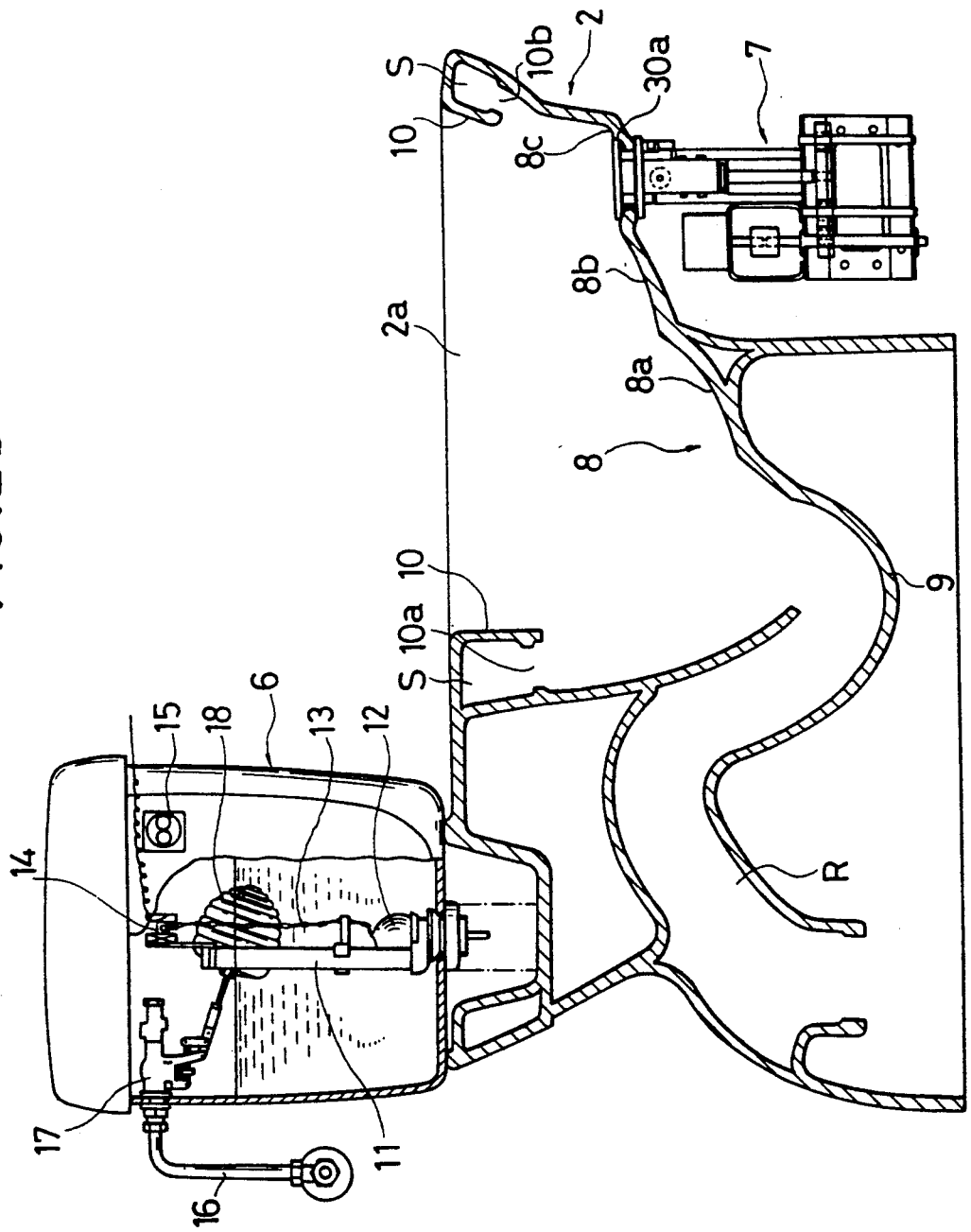

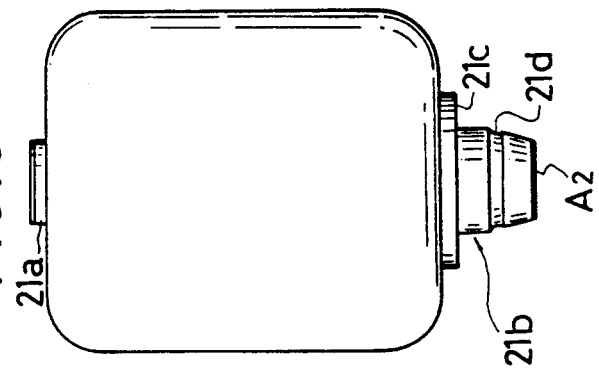
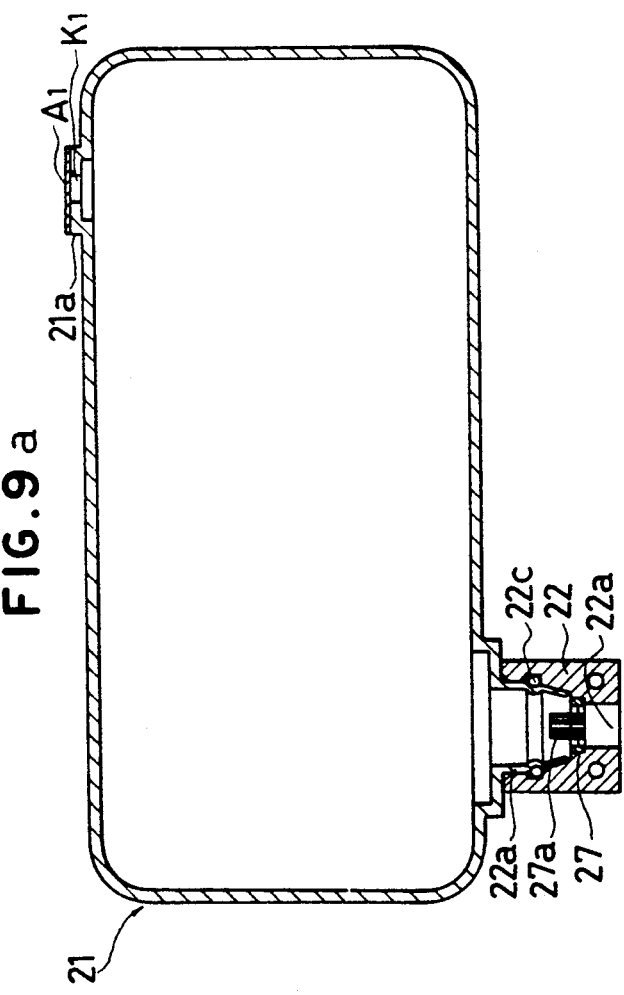
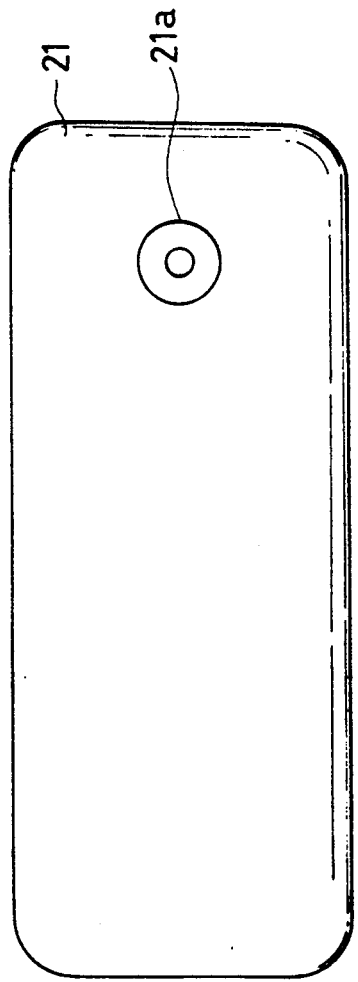

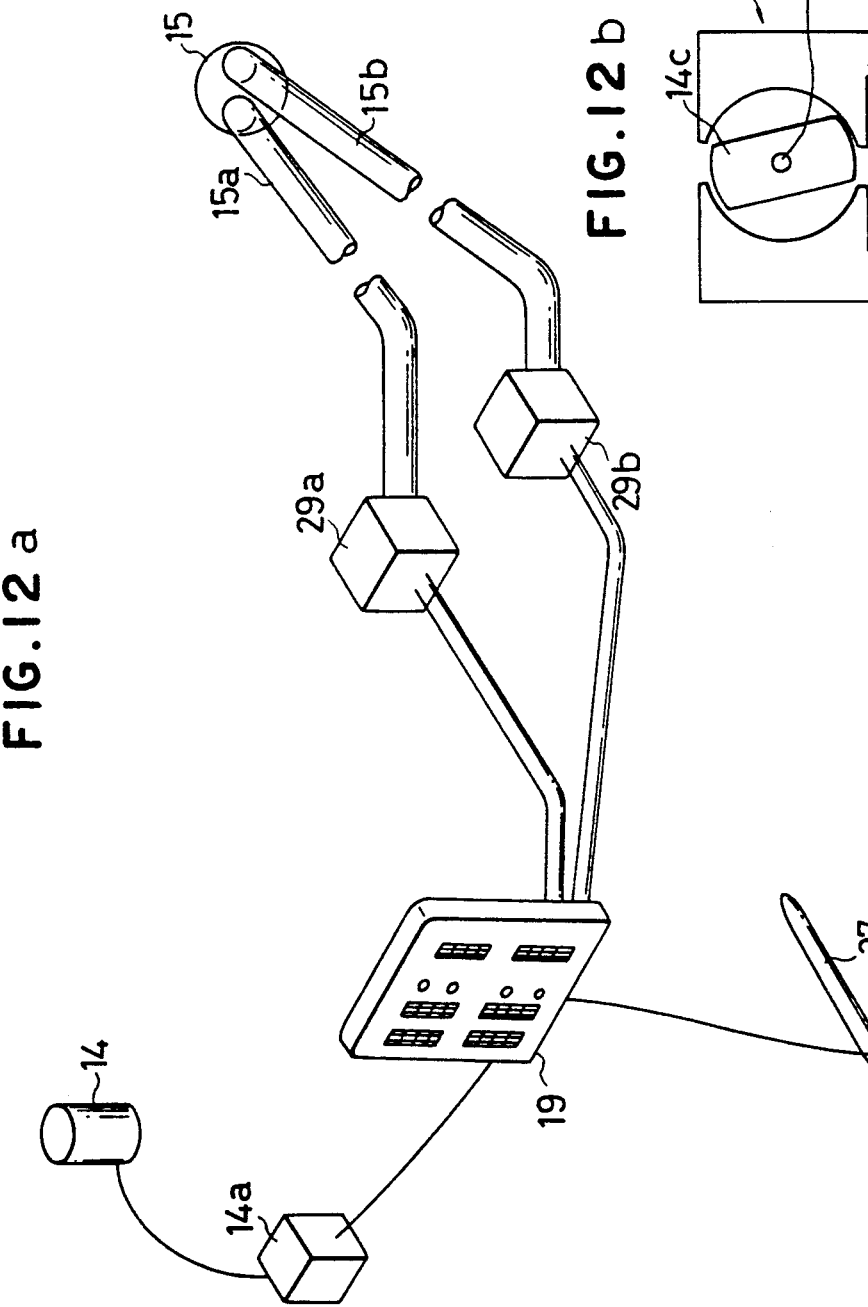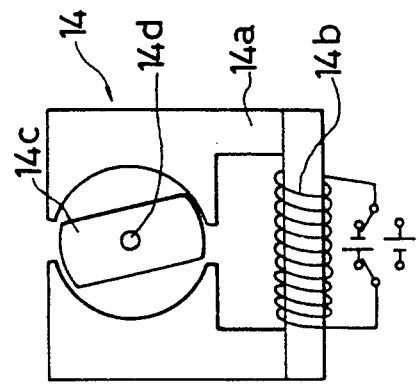

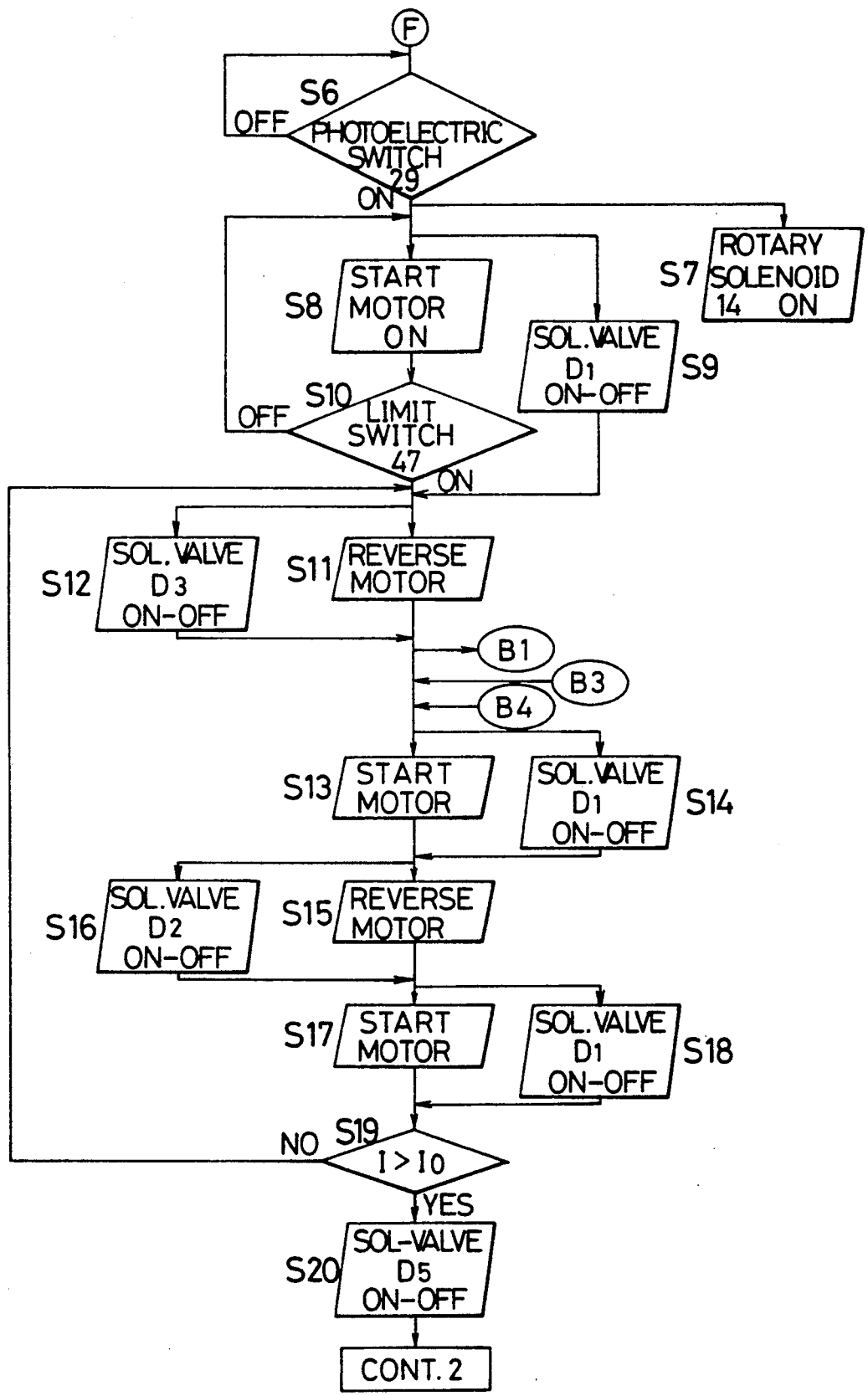

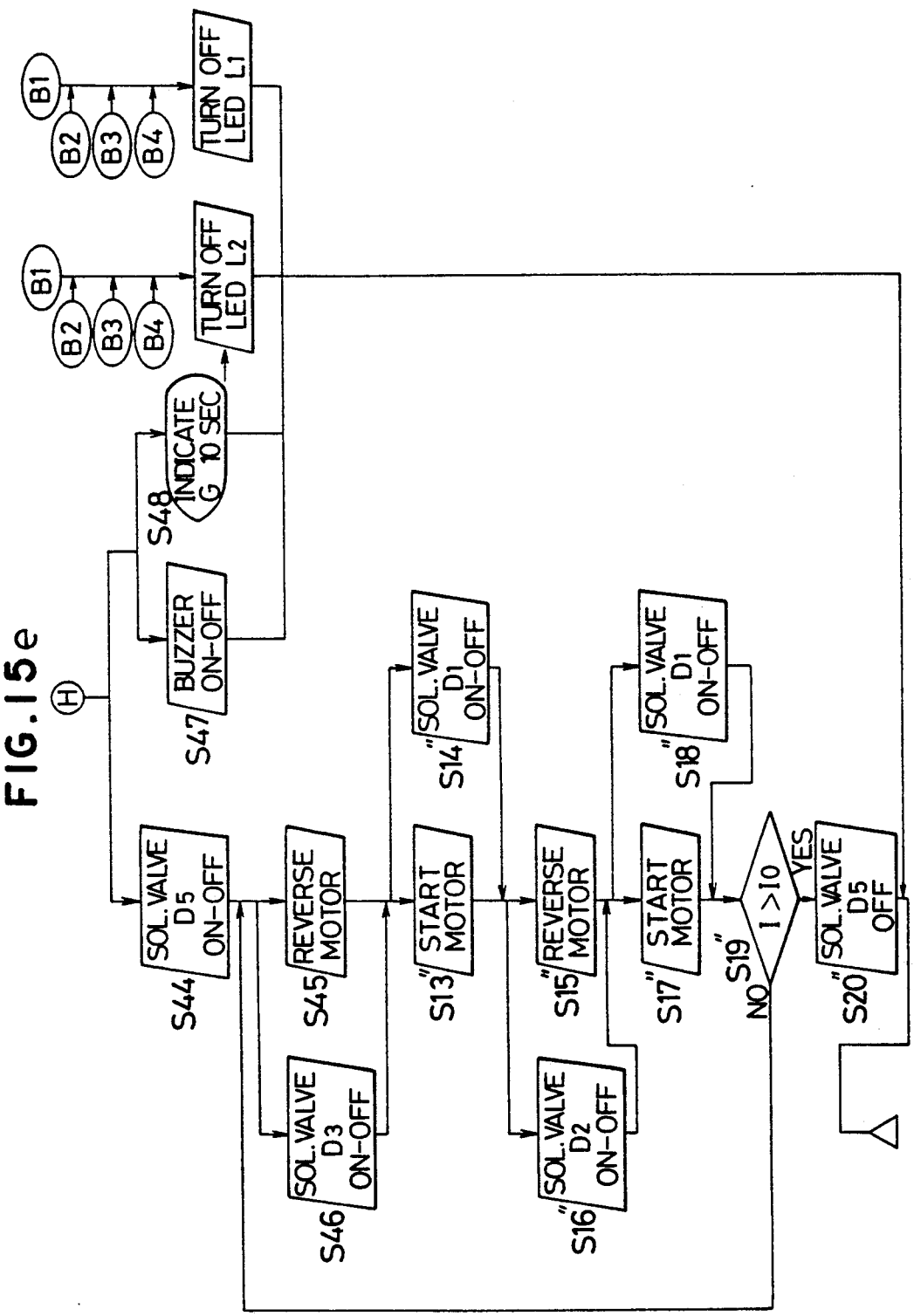

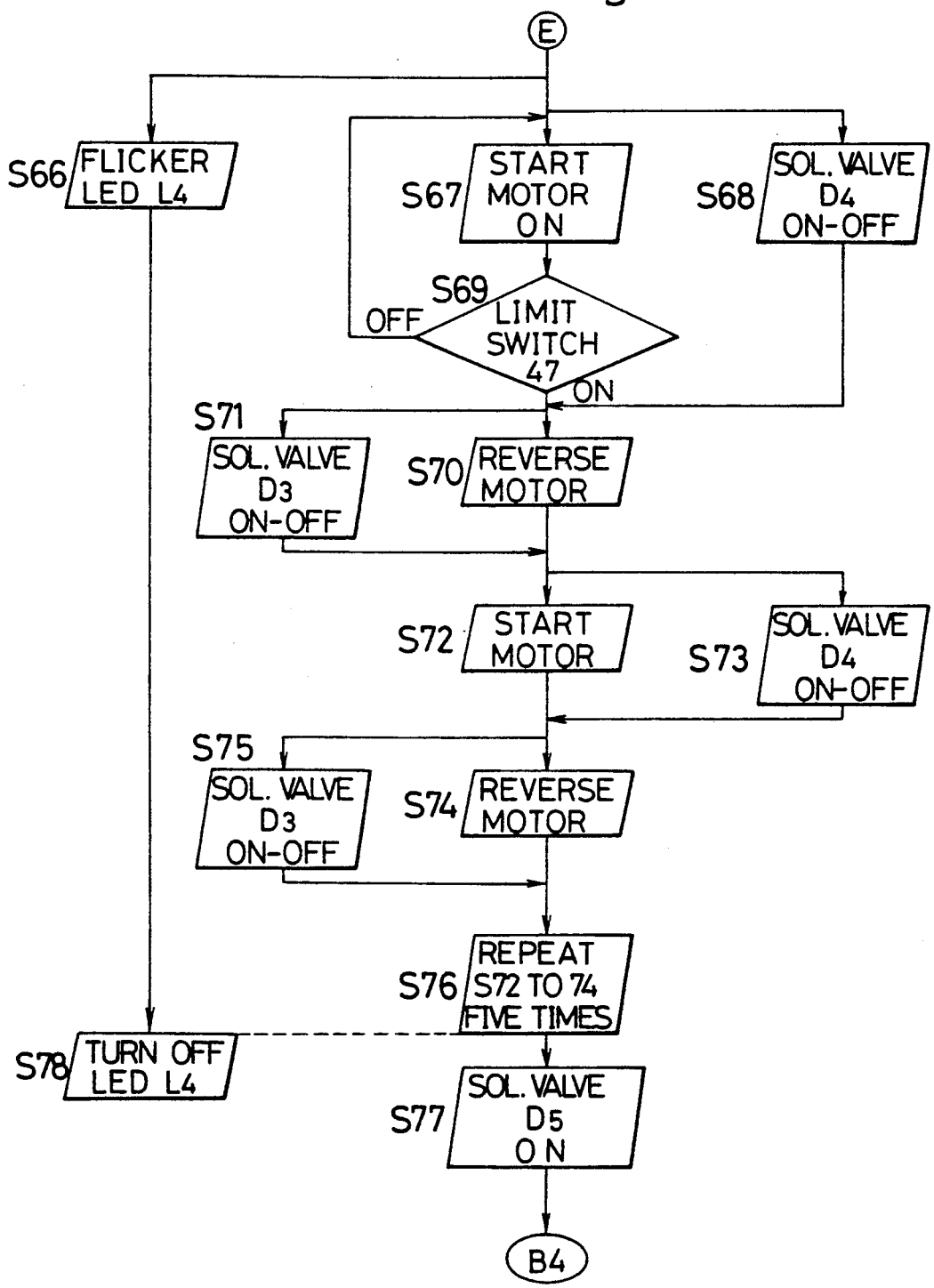

SYSTEM FOR COLLECTING INFORMATION ON HEALTH

This is a division of application Ser. No. 195,557, filed May 18, 1988, now U.S. Pat. No. 4,982,741.

BACKGROUND OF THE INVENTION

1. Field of the Invention

This invention relates to an apparatus for determining the concentration of sugar, bilirubin, and other substances in urine during its excretion to thereby obtain information which enables certain judgment as to the condition of health, and also to a toilet stool equipped with such an apparatus. This invention also relates to a system for collecting information on health which includes such a toilet stool.

2. Description of the Prior Art

The examination of urine for glucose is made for the diagnosis of diabetes mellitus, etc. The examination of urine for bilirubin is made for ascertaining the function of the kidney. These examinations are usually made by medical specialists at hospitals, or other special organizations. It has been difficult to examine urine for sugar or bilirubin at home.

There is known a toilet stool having a testing portion which contains a reagent. If urine is discharged into the testing portion, it reacts with the reagent and causes it to present a change of color which indicates the presence of sugar in the urine. This stool, however, makes it possible to know only the presence of sugar, etc. in the urine as a result of a change of color. It is of no use for determining the concentration of glucose, etc. accurately. It is not always possible to expect the proper reaction of the reagent and the urine. It is not always possible to expect that the testing portion contains a sufficient supply of reagent. As a large amount of urine which is discharged is directly brought into contact with the reagent, it is often likely that the reagent may not bring about a proper oxidizing action, but may present a wrong change of color. Moreover, it is often the case that the reagent and the urine which have been reacted in the testing portion are not washed away completely. Therefore, the known apparatus is not accurate or reliable.

There are a variety of medical instruments which are easy to use, including an electronic thermometer, a scale and an automatic sphygmomanometer. They are all conveniently designed for personal use. The data obtained by using any such instrument are, however, usually left to his own judgment. Nobody can derive any professional conclusion from the data unless he is a medical specialist. Even if one measures his temperature, weight and blood pressure, he cannot derive any comprehensive conclusion based on the combination of those data unless he has any professional knowledge.

OBJECTS OF THE INVENTION

It is an object of this invention to provide an apparatus which enables the automatic and accurate detection of certain substances in urine.

It is another object of this invention to provide a toilet stool including an apparatus which enables the automatic and accurate detection of certain substances in urine.

It is still another object of this invention to provide a system which can collect certain information on the health of a patient from his urine and transfer it to a hospital, etc., so that a doctor may diagnose certain cases without seeing the patient personally.

BRIEF DESCRIPTION OF THE DRAWINGS

FIG. 2a is a vertical sectional view of the main body of the toilet stool shown in FIG. 1;

FIG. 2b is a view similar to FIG. 2a, but showing a water receptacle, too;

FIG. 6b is a top plan view of FIG. 6a;

FIG. 6c is a bottom plan view of FIG. 6a;

FIG. 9a is a vertical sectional view of a cartridge holding a reagent;

FIG. 9b is a top plan view of the cartridge;

FIG. 9c is a side elevational view

FIG. 12a is a diagram showing the wiring connections between a photoelectric switch and a rotary solenoid;

FIG. 12b is a schematic view of the rotary solenoid;

FIGS. 15a to 15g are flow charts for showing control programs for the urine sampling device;

SUMMARY OF THE INVENTION

Figure 1:
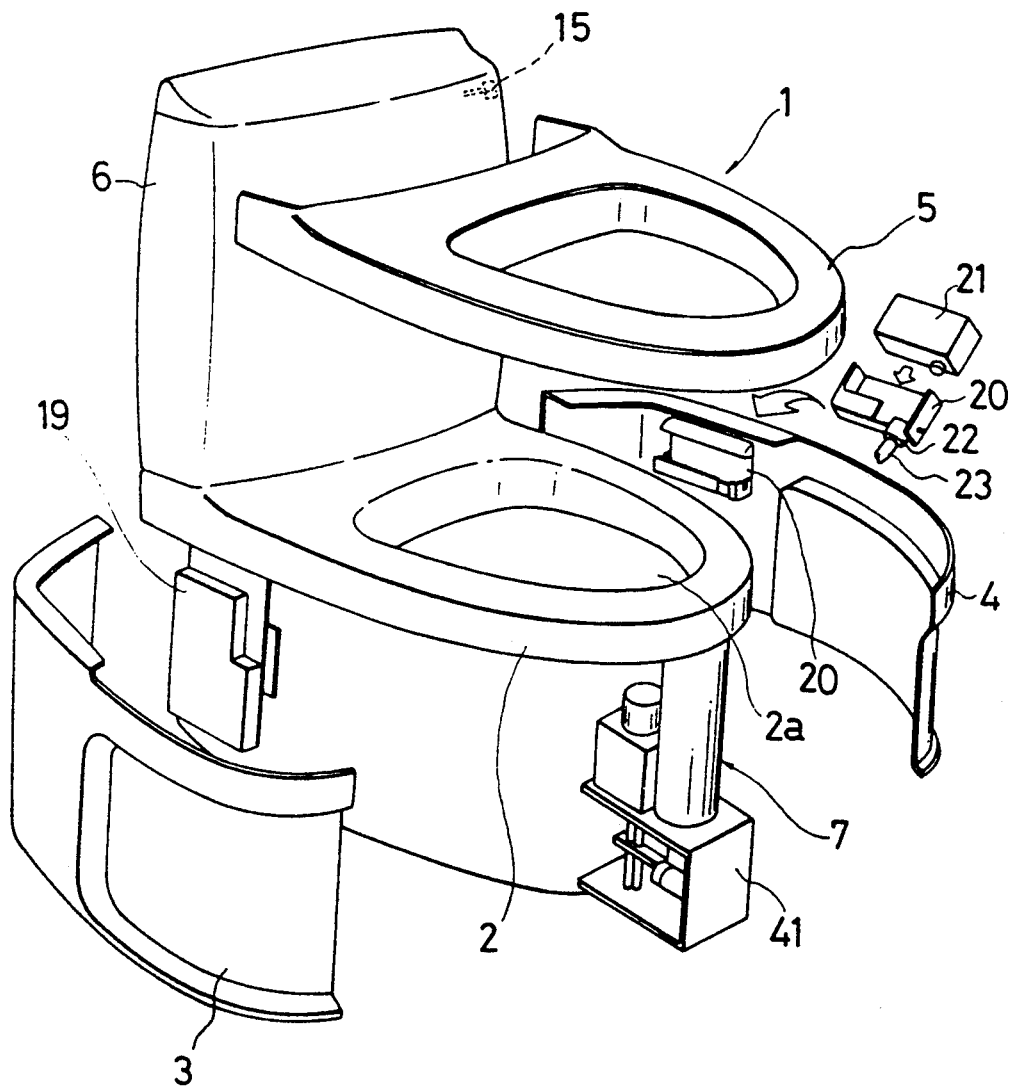
FIG. 1 is an exploded perspective view of a toilet stool embodying this invention.

The apparatus of this invention for detecting certain substances in urine includes a vertically disposed cylinder having at its upper end an opening defining an inlet for urine. The cylinder includes an upper portion having an inside diameter which is larger than that of its remaining portion. The apparatus also includes a piston fitted in the cylinder, a mechanism for moving the piston vertically, and an electrode extending into the cylinder through the wall of its diametrically enlarged upper portion and having an inner end adapted to contact a liquid in the cylinder to determine the concentration of its constituents. The apparatus further includes a reagent supplying device which comprises a reservoir for a reagent connected through a pipeline and a pump to an opening made in the wall of the upper portion of the cylinder, and a valve provided in the pipeline so that the reagent may be supplied into the cylinder when the valve is opened, and a water supplying device which comprises a source of water supply connected through a pipeline to an opening made in the wall of the upper portion of the cylinder, and a valve provided in the pipeline so that water may be supplied into the cylinder when the valve is opened.

The apparatus may further include a device for operating the values which have been determined by the electrode. The apparatus may also include a device for displaying the results of operation by the operating device.

The apparatus may further include a control device which ensures that a series of steps occur properly in accordance with the following sequence:

lowering the piston to its lowermost position to enable the cylinder to receive urine;

raising the piston to its uppermost position so that the urine may stay only in the space between the piston and the diametrically enlarged upper portion of the cylinder; and supplying appropriate amounts of water and reagent into the cylinder, while lowering the piston to its lowermost position, as well as calculating the concentrations of certain constituents of the urine in accordance with the signals transmitted from the electrode and displaying them.

The toilet stool of this invention includes a bowl having an inner surface in which the apparatus as hereinabove described is exposed to receive a part of the urine which is discharged into the bowl.

The system of this invention for collecting information on health comprises an apparatus for analyzing urine for glucose etc., a data operating and transmitting computer which receives the results of analysis from the analyzing apparatus operates then appropriately and transmits the resulting data, and a data receiving and recording computer which receives the data from the data operating and transmitting computer and records them successively.

The system may alternatively comprise an instrument for determining temperature, an instrument for determining weight, an instrument for determining blood pressure, an apparatus for analyzing urine, an interface circuit for converting the results of determination and analysis from analog to digital data, a first computer which receives data from the interface circuit, operates them appropriately and transmits them, and a second computer which receives the data from the first computer and records them successively.

The reagent which is employed by the apparatus of this invention is an enzymic reagent which reacts with certain constituents of urine. The result of their reaction is outputted by the electrode as an electrical signal which makes it possible to determine the concentration of sugar, etc. in the urine numerically. The apparatus no longer relies upon any change of color. Therefore, it can very accurately determine the condition of a person's health by examining his urine.

The toilet stool of this invention facilitates the examination of one's urine drastically, as it enables the automatic determination of its constituents only if he turns on a number of switches, sits down and discharges urine.

If anybody who uses the system of this invention sends information on his health to his home doctor through the computers every day, he can have his health examined by his doctor every day without going to the hospital. The system enables a doctor to examine a large number of patients within a short time, since he can derive his medical advice from the transmitted data without having to see each patient personally in his consultation room.

DETAILED DESCRIPTION OF THE INVENTION

Figure 3:
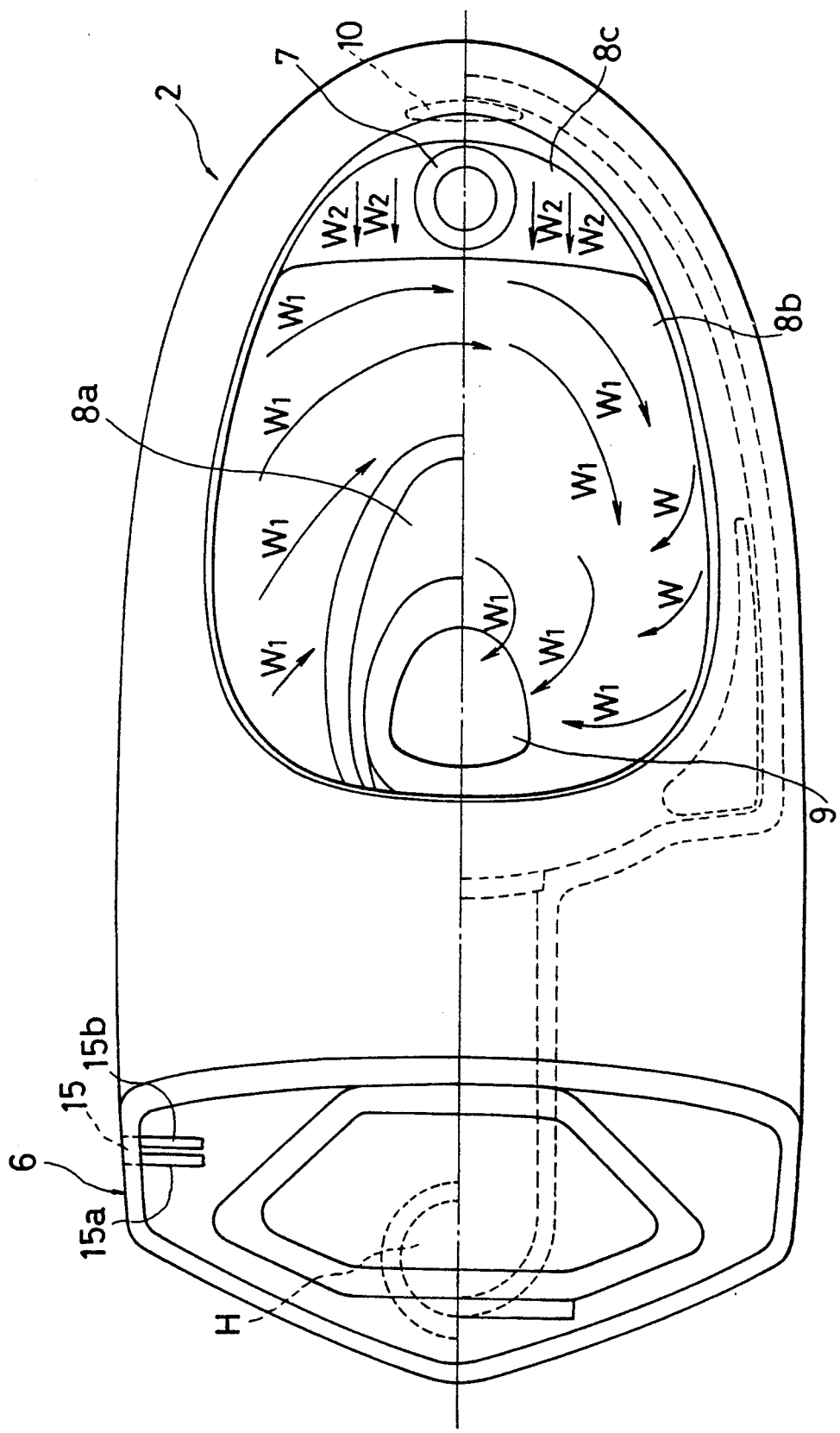
FIG. 3 is a top plan view of FIG. 2b.

A toilet stool embodying this invention is shown in FIGS. 1 to 3. The toilet stool 1 comprises a main body 2 having a top opening 2a, a left side cover 3, a right side cover 4, a top cover 5, and a flushing cistern 6 upstanding from the rear end of the main body 2. The toilet stool 1 is, thus, substantially identical in general construction to any conventionally known toilet stool.

According to a salient feature of this invention, the toilet stool 1 is provided with a urine sampling device 7 below the front end of its main body 2. The main body 2 defines a bowl 8 having a water trap 9 at its bottom. The bowl 8 has an inner surface which includes a curved and inclined first surface portion 8a which is contiguous to the upper edge of the trap 9, a curved and inclined second surface portion 8b which is contiguous to the upper edge of the first surface portion 8a, and a horizontal third surface portion 8c which is contiguous to the upper edge of the second surface portion 8b, as shown in FIG. 2a or 2b. The main body 2 has a rim 10 defining the edge of the top opening 2a and having a portion positioned above the third surface portion 8c of the bowl 8. The rim 10 is so shaped as to form a hollow interior defining a water passage S which is connected to the cistern 6, so that flushing water may flow down into the water passage S. The rim 10 has at its bottom apertures 10a and 10b through which flushing water is allowed to flow down into the bowl 8. A drain R is connected to the trap 9 for removing human waste and other filthy matter therefrom. The urine sampling device 7 has a top exposed in the third surface portion 8c of the bowl 8, as shown in FIGS. 2a and 2b. Further details of the device 7 will be set forth later.

The flushing cistern 6 contains an upright overflow pipe 11, as shown in FIG. 2b. The overflow pipe 11 is provided at its lower end with a water passageway which is connected to the water passage S. The water passageway is normally closed by a ball valve 12. A chain 13 has one end fastened to the ball valve 12. The chain 13 is also connected to the rotary shaft 14d of a rotary solenoid 14 (see FIG. 12b) adjacent to the top of the cistern 6.

Figure 10:
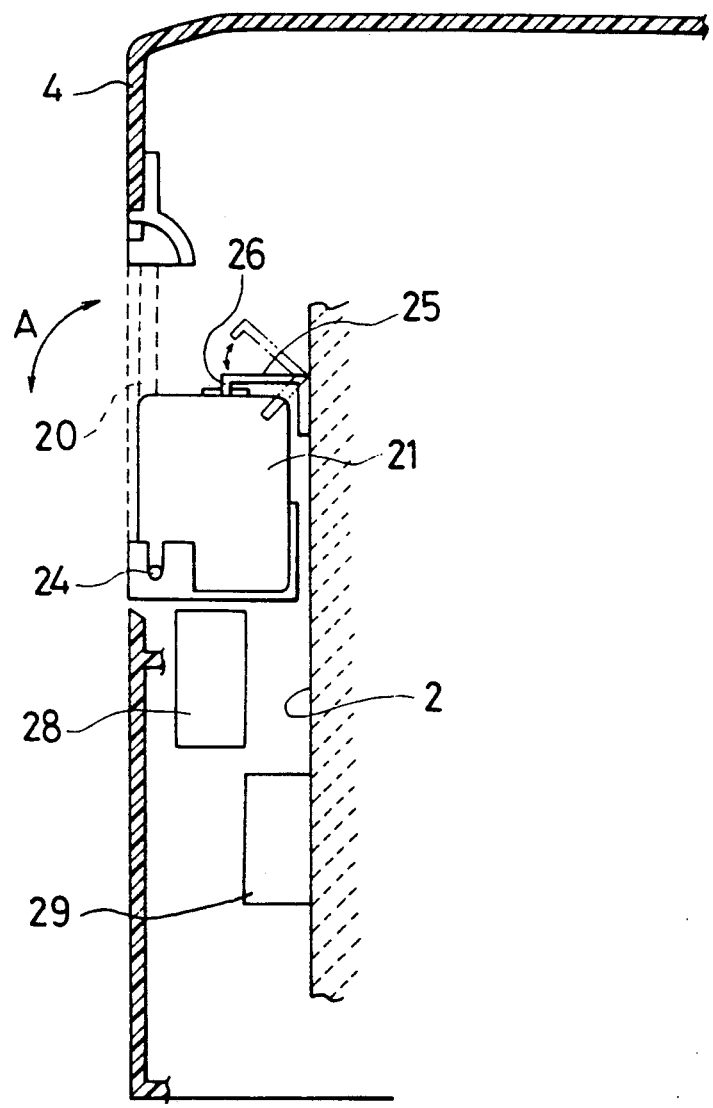
FIG. 10 is a fragmentary cutaway view of a bowl cover on which the cartridge is supported.

A photoelectric switch 29 is provided between the main body 2 and the right side cover 4 and is supported on the main body 2 near its bottom, as shown in FIG. 10. A detector 15 is fitted in the wall of the cistern 6 near the rotary solenoid 14, as shown in FIG. 2b. Two tubular optical fibers 15a and 15b are connected to the detector 15 and extend through the cistern 6. A light emitter 29a and a light receiver 29b are connected to the lower ends of the optical fibers 15a and 15b, respectively. The light emitter 29a is adapted to radiate red light through the optical fiber 15a and from the sidewall of the cistern 6.

The overall arrangement of the photoelectric switch 29 is shown in FIG. 12a. If the user of the toilet stool puts his hand in the red light emitted from the end of the optical fiber 15a through a lens, etc., the light which is reflected by the hand enters the optical fiber 15b opening in the detector 15, through a lens, etc., and is transmitted therethrough to the light receiver 29b which comprises a photodiode, etc., whereby the presence of the user's hand is detected. The photoelectric switch 29 outputs a signal to a control panel 19 which comprises a microcomputer connected to the photoelectric switch 29. The control panel 19 outputs a signal to a solenoid driving circuit 14a to actuate the rotary solenoid 14. Its rotary shaft 14d is rotated by an angle of about 90° to wind up the chain 13, whereby the ball valve 12 is lifted to open the water passageway, so that water may flow down from the cistern 6 into the bowl 8 through the water passage S to flush the bowl 8 and the drain R.

The rotary solenoid 14 comprises an electromagnetic portion 14a formed in the shape of a frame, energizing the electromagnetic portion 14a, a rotor 14c comprising a magnet disposed rotatably in the electromagnetic portion 14a, and a rotary shaft 14d projecting from the center of the rotor 14c, as shown in FIG. 12b. If an electric current is supplied to the coil 14b, the electromagnetic portion 14a is energized to rotate the rotor 14c by an angle of about 90° and the rotary shaft 14d is, therefore, rotated to raise the chain 13.

The cistern 6 is provided with a ball tap 17 which is connected to a water pipe 16 for supplying water into the cistern 6. The ball tap 17 is opened and closed by a float 18, so that an appropriate level of water may always be maintained in the cistern 6.

If the rotary solenoid 14 is actuated to supply flushing water into the bowl 8, the water which flows down through the aperture 10a in the rim 10 forms a swirl as shown by arrows $W_1$ in FIG. 3. It flushes the first and second surface portions 8a and 8b of the bowl 8 and eventually flows down into the trap 9. A minor portion of the water which has been supplied from the cistern 6 flows down through the other aperture 10b at the front end of the stool, flushes the third surface portion 8c of the bowl 8 as shown by arrows $W_2$ and is eventually absorbed into the swirl $W_1$. Although a part of the swirl $W_1$ may flow over the third surface portion 8c, that part of the swirl $W_1$ which flows along the third surface portion 8c and is, therefore, likely to flow over it does not contain waste. Therefore, it does not contaminate the third surface portion 8c, but it is always kept clean. Therefore, only urine and water enter the urine sampling device 7 and no waste, other than urine, enters it.

The right side cover 4 has near its rear end an opening in which a cartridge holder 20 is mounted, as shown in FIGS. 1 and 10. The cover 4 is provided with a pin 24 on which the cartridge holder 20 is supported vertically rotatably as shown by an arrow A in FIG. 10. The cartridge holder 20 is rotatable to have its upper end project outwardly and thereby receive a reagent cartridge 21 therein.

The cartridge 21 is a totally closed rectangular case, as shown in FIGS. 9a to 9c. It is made of a resin and holds an enzylic reagent. It has a top projection 21a defining an air port $K_1$ closed by an aluminum foil $A_1$ which is removed when the cartridge 21 is used. It also has a bottom projection 21b defining a connector which is also hollow and is closed by an aluminum foil $A_2$ which is also removed when the cartridge 21 is used. The bottom projection 21b is provided with a flange 21c and is encircled by a groove 21d.

The cartridge holder 20 is provided with a socket 22 and one end of a hose 23 is connected to the socket 22, as shown in FIG. 1. The socket 22 is provided with a fitting 27 having a central pin 27a, as shown in FIG. 9a. The socket 22 has a connecting bore 22b in which the bottom projection 21b of the cartridge 21 is received when the cartridge 21 is fitted in the holder 20. The socket 22 is also provided with a holding ring 22c which fits in the groove 21d to hold the projection 21b in position, as shown in FIG. 9a. The socket 22 also has a reagent guide bore 22a formed on the opposite side of the pin 27a from the connecting bore 22b. When the projection 21b is inserted into the socket 22 as hereinabove described, the aluminum foil $A_2$ is broken by the pin 27a, so that the reagent may flow down through the pin 27a and the bore 22a into the hose 23. The other end of the hose 23 is connected to a reagent pipe $Y_6$ in the urine sampling device 7.

If the cartridge holder 20 is rotated back to its closed position, the cartridge 21 is withdrawn into the space between the main body 2 and the right side cover 4, as shown in FIG. 10. A substantially L-shaped bar 25 is rotatably supported on the main body 2, as shown in FIG. 10. The bar 25 is provided at its upper end with a needle 26 projecting therefrom at right angles thereto. When the cartridge 21 is withdrawn into the space inwardly of the cover 4, it abuts on the bar 25 and causes it to rotate downwardly, whereupon the needle 26 is moved down to pierce the aluminum foil $A_1$ covering the top projection 21a of the cartridge 21 and open the air port $K_1$, so that air may be admitted into the cartridge 21 to enable the reagent to flow down through the socket 22 smoothly.

A proximity switch 28 is mounted on the inside of the cover 4 below the cartridge holder 20, as shown in FIG. 10. The proximity switch 28 is provided for checking the presence of the reagent in the cartridge 21. When all of the reagent in the cartridge 21 has been consumed, the proximity switch 28 outputs a corresponding signal to the control panel 19.

The light emitter and receiver 29a and 29b of the photoelectric switch 29 are located near the proximity switch 28 and inwardly of the cover 4. The control panel 19 is supported on the main body 2 adjacent to its rear end and is covered by the left side cover 3.

Figure 4:
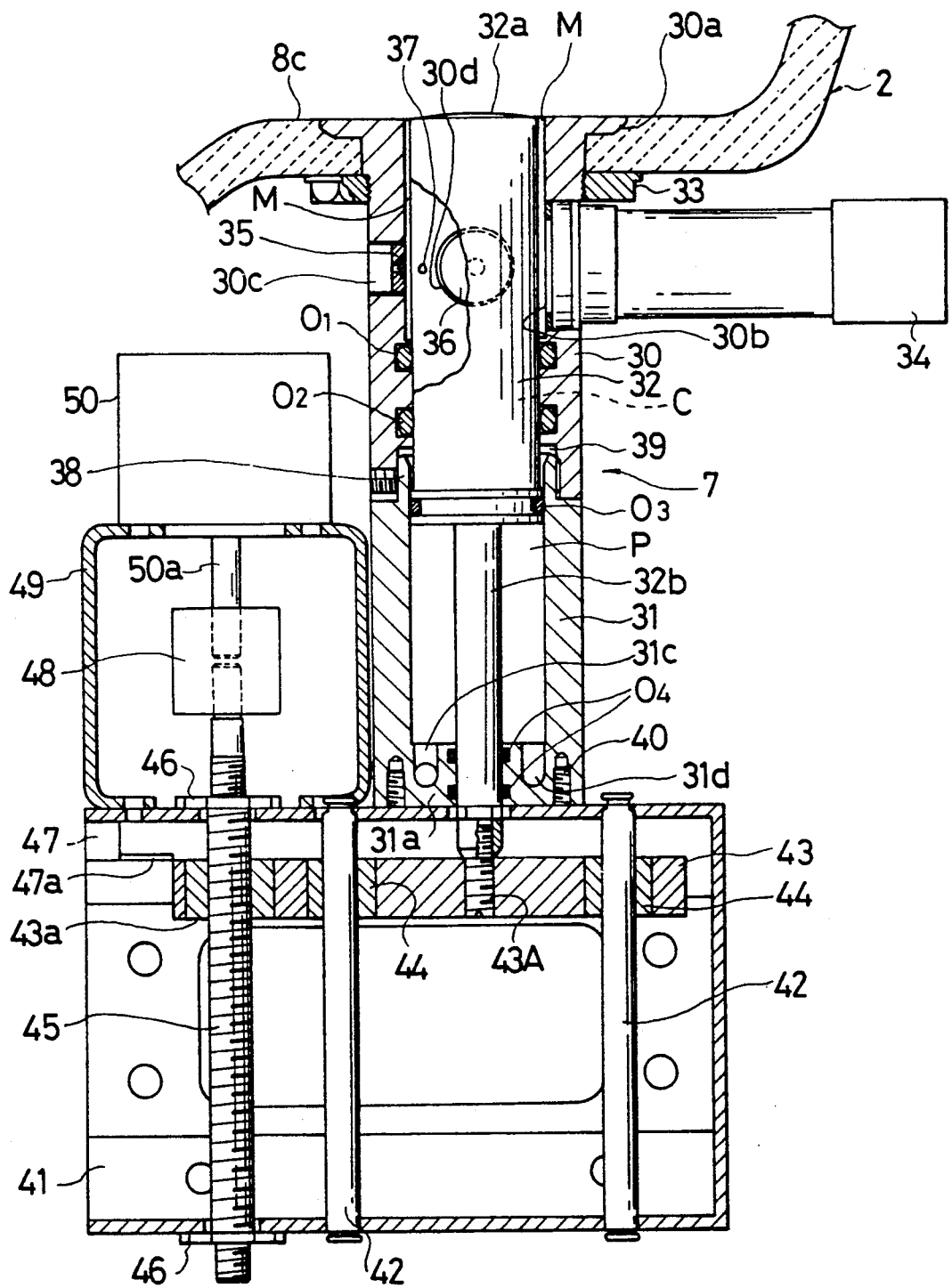
FIG. 4 is a longitudinal sectional view of a urine sampling device.
Figure 5:
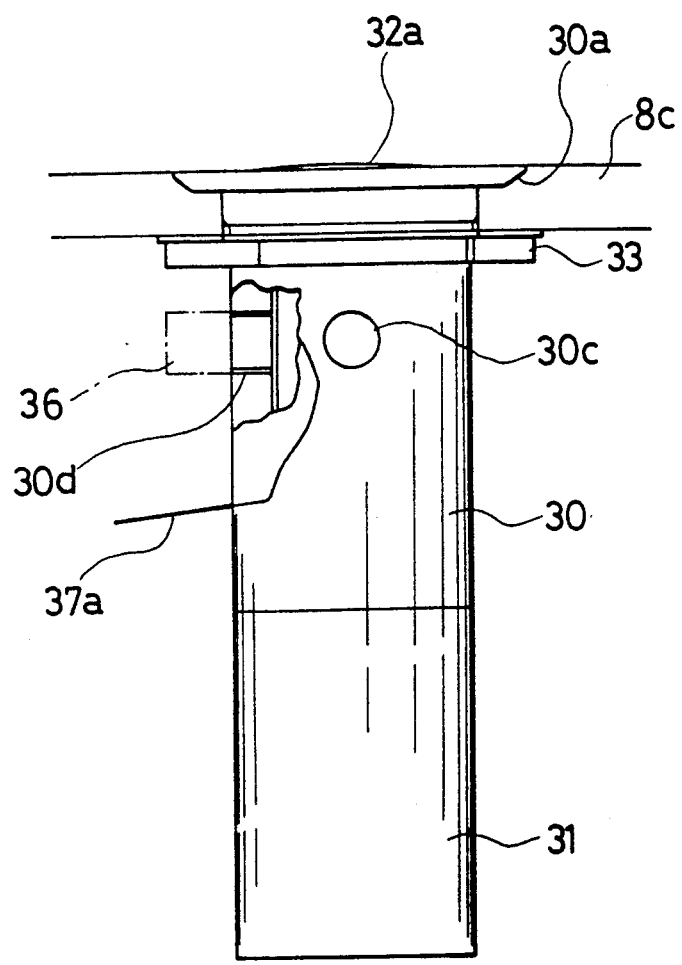
FIG. 5 is a fragmentary side elevational view of the device shown in FIG. 4.

Reference is now made to FIGS. 4 to 8c showing the urine sampling device 7 in detail. It includes an upright urine sampling cylinder 30, an upright pump cylinder 31 connected to the lower end of the urine sampling cylinder 30 coaxially therewith, and an upright piston 32 which is vertically slidable in the cylinders 30 and 31. The urine sampling cylinder 30 is provided at its upper end with a radially outwardly projecting flange 30a which is substantially flush with the third surface portion 8c of the bowl 8, as shown in FIG. 4. The flange 30a is embedded in the wall of the main body 2. The cylinder 30 has a threaded outer surface portion 30f below the flange 30a and a nut 33 is screwed onto the threaded outer surface portion 30f. The wall of the main body 2 is held between the flange 30a and the tightened nut 33, whereby the urine sampling device 7 is secured to the main body 2.

The cylinder 30 has a hollow interior defining a cylindrical urine sampling chamber C. The cylindrical wall of the cylinder 30 is provided therethrough with an electrode connecting port 30b, a nozzle hole 30c which is diametrically opposite to the port 30b, a spray hole 30d located at an angle of 90° to each of the port 30b and the hole 30c, and a thermistor hole 30e. An oxygen electrode 34 is threadedly connected in the electrode connecting port 30b. A nozzle member 35 is threadedly fitted in the nozzle hole 30c. A washing spray 36 is threadedly connected in the spray hole 30d. A rod-shaped thermistor 37 is inserted in the thermistor hole 30e.

The oxygen electrode 34 is provided for outputting the amount of oxygen which is consumed by an enzyme when an oxidizing reaction takes place between the enzymic reagent and glucose in the urine, as a value of electric current based on a variation of resistance between the electrodes.

Figure 8A:
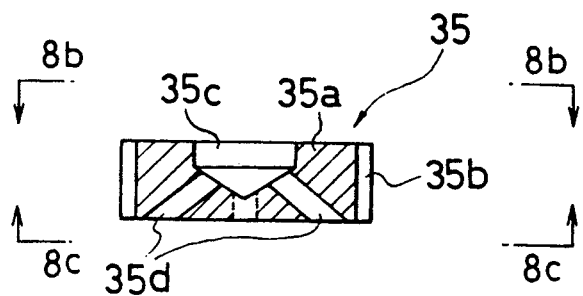
FIG. 8a is an axial sectional view of a nozzle member connected threadedly to the urine sampling cylinder shown in FIG. 4.
Figure 8B:
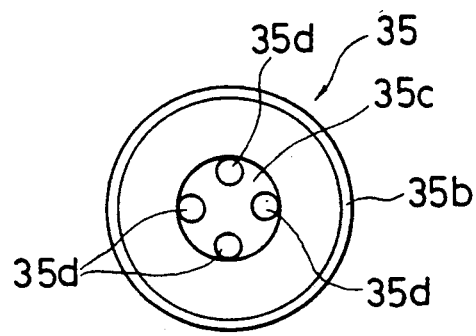
FIG. 8b is a top plan view of the nozzle member.
Figure 8C:
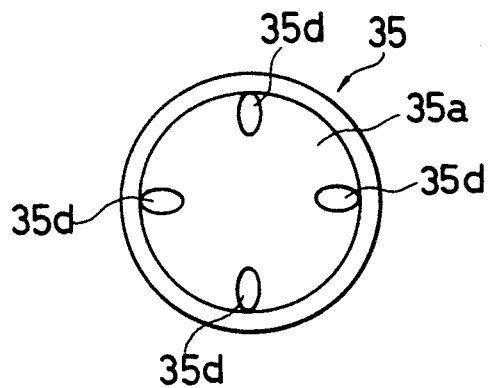
FIG. 8c is a bottom plan view thereof.

The nozzle member 35 comprises a disk, or short cylinder 35a having an outer peripheral surface formed with a screw thread 35b, as shown in FIGS. 8a to 8c. The disk 35a has a conical hole 35c opening in the center of one surface thereof. The disk 35a also has four spreading holes 35d each having one end connected to the conical hole 35c and extending radially outwardly, while the other end of each hole 35d opens in the other surface of the disk 35a. If a liquid, such as a reagent or diluting water, is supplied into the conical hole 35c, it is radially spread through the spreading holes 35d and jetted out into the urine sampling chamber C.

The inner surface of the cylinder 30 is provided with two vertically spaced apart O-ring grooves 30g and 30h. Two O-rings $0_1$ and $0_2$ are fitted in the O-ring grooves 30g and 30h, respectively, to maintain a liquid-tight seal between the inner surface of the cylinder 30 and the peripheral surface of the piston 32. The wall of the cylinder 30 is provided therethrough below the lower O-ring groove 30h with a plurality of apertures 39 which allow for the escape of air compressed between the O-ring $0_2$ in the groove 30h and an O-ring $0_3$ fitted about the piston 32 when the piston 32 is vertically moved in the cylinder 30, so that the piston 32 may be smoothly movable.

The cylinder 30 has an upper portion and a lower portion. The upper portion has an inside diameter which is larger than that of the lower portion, so that a clearance M may be formed between the inner surface of the upper portion of the cylinder 30 and the outer peripheral surface of the piston 32 when the piston 32 is raised, as shown in FIG. 4.

The pump cylinder 31 has a hollow interior defining a cylindrical pump chamber P. It has an upper end portion inserted in the lower end portion of the urine sampling cylinder 30. The wall of the cylinder 30 is provided therethrough adjacent to its lower end with a threaded hole 30i in which a screw 38 is threadedly engaged to hold the two cylinders 30 and 31 together.

Figure 6A:
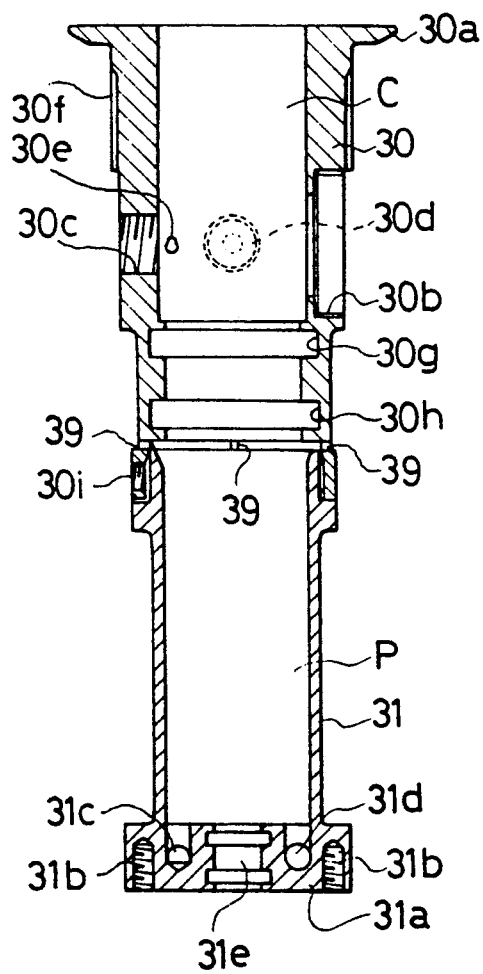
FIG. 6a is a longitudinal sectional view of a urine sampling cylinder and a pump cylinder in the device shown in FIG. 4.
Figure 6B:
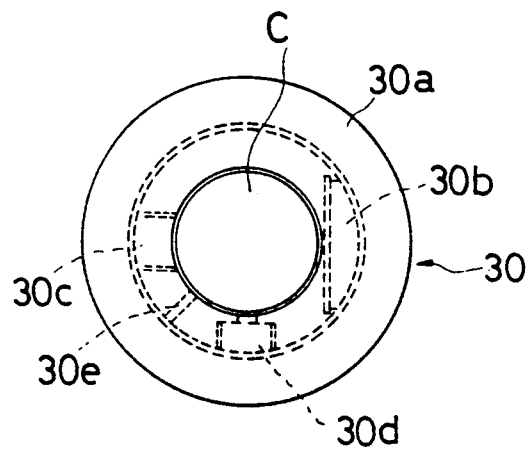
Figure 6C:
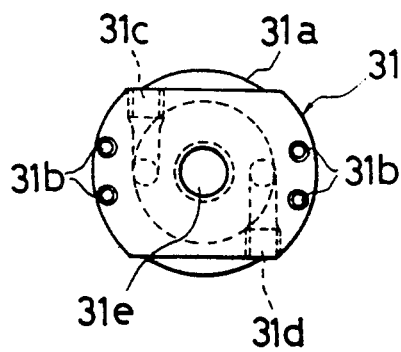

The pump cylinder 31 has a base 31a closing its lower end substantially, as shown in FIG. 4 or 6a. The base 31a is axially provided therethrough with a piston rod hole 31e, as shown in FIG. 6a or 6c, and a piston rod 32b extends slidably therethrough, as shown in FIG. 4. Two vertically spaced apart O-rings $0_4$ are fitted in the base 31a coaxially with the hole 31e and encircle the piston rod 32b, as shown in FIG. 4. The base 31a is also provided with two parallel L-shaped ports 31c and 31d having a diametrically opposite relation to each other and each located on the opposite side of the central hole 31e from the other, as shown in FIG. 6c. Each of the L-shaped ports 31c and 31d consists of a horizontal portion and a vertical portion having a lower end connected to the inner end of the horizontal portion and an upper end opening to the pump chamber P, as shown in FIGS. 6a and 6c. The horizontal portions of the ports 31c and 31d lie in a mutually staggered relation and the outer ends thereof open in the peripheral surface of the base 31a in a diametrically opposite relation to each other, as shown in FIG. 6c. One of the ports, 31c, is provided for introducing diluting water into the pump chamber P and the other port 31d is used for introducing a reagent. The base 31a is provided along its outer edge with four threaded holes 31b, and a screw 40 is inserted in each hole 31b for securing the pump cylinder 31 to a base frame 41 for the urine sampling device 7, as shown in FIG. 4.

A pair of parallel guide bars 42 are vertically fixed in the base frame 41 and a table 43 is vertically slidably supported on the guide bars 42. The table 43 is supported on each guide bar 42 by a linear bearing 44 which ensures the smooth vertical movement of the table 43. A vertical screw shaft 45 is provided in the base frame 41 in parallel to the guide bars 42. A pair of vertically spaced apart ball bearings 46 are attached to the base frame 41 for supporting the screw shaft 45 near its upper and lower ends, respectively, so that the screw shaft 45 may be rotatable about its own axis. A motor frame 49 is mounted on the base frame 41. The upper end of the screw shaft 45 is located in the motor frame 49. A stepping motor 50 is mounted on the motor frame 49 and has a downwardly extending output shaft 50a located in the motor frame 49. The screw shaft 45 and the output shaft 50a are coaxial with each other and the upper end of the screw shaft 45 is connected to the lower end of the output shaft 50a by a joint 48 in the motor frame 49. The screw shaft 45 has a screw thread cut on it and a nut 43a screwed on the screw shaft 45 is secured to the table 43. The piston rod 32b has an upper end connected to the piston 32 and a lower end connected to the table 43 by a screw 43A.

If the motor 50 is driven, its rotation is transmitted to the screw shaft 45 through the output shaft 50a and the joint 48 to cause the screw shaft 45 to rotate about its own axis. The rotation of the screw shaft 45 causes the vertical movement of the nut 43a and therefore of the table 43 along the guide bars 42. The vertical movement of the table 43 results in the vertical movement of the piston rod 32b and the piston 32 in the urine sampling cylinder 30 and the pump cylinder 31.

A limit switch 47 is provided on the base frame 41 adjacent to its top for detecting the arrival of the table 43 at its uppermost position. The limit switch 47 is electrically connected to the control panel 19.

Figure 7:
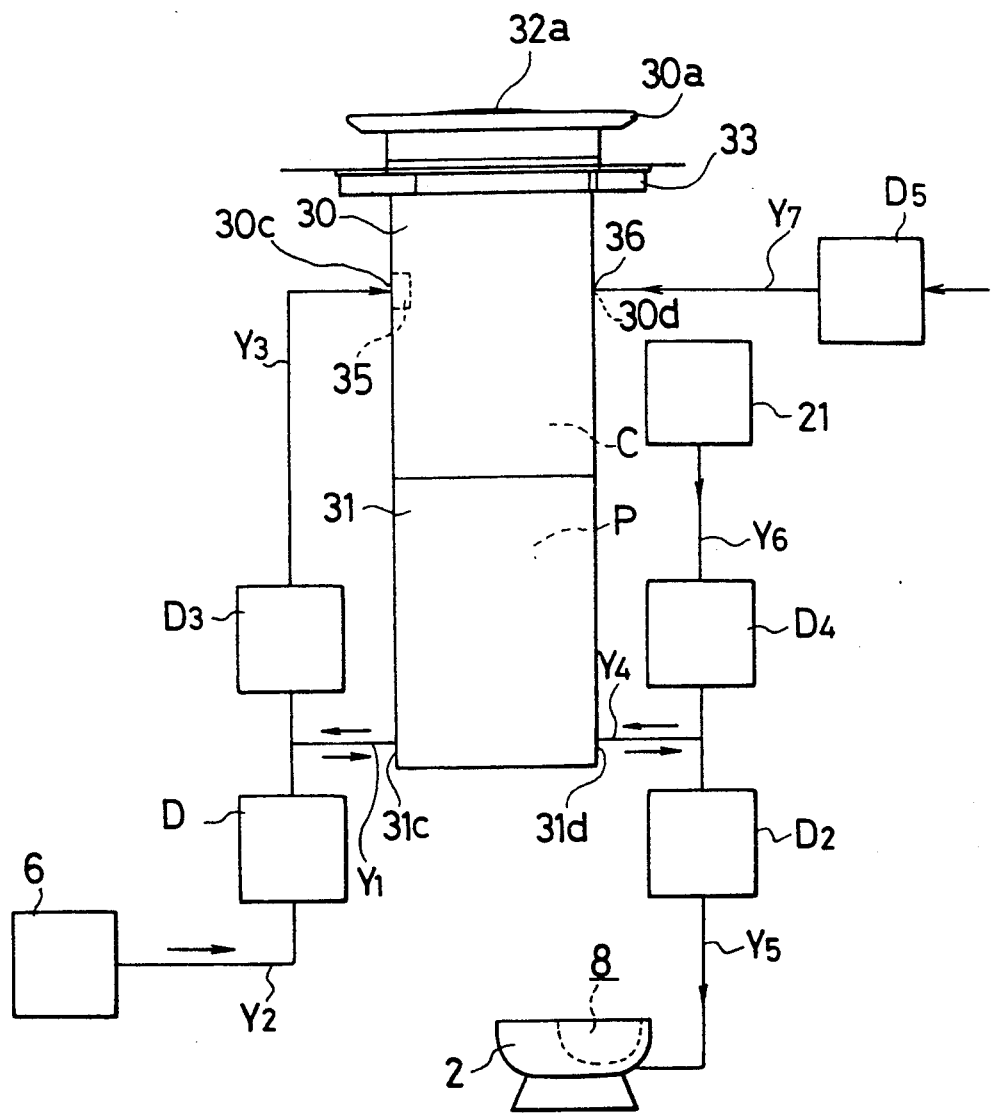
FIG. 7 is a piping diagram for the urine sampling pump cylinders.

Reference is now made to FIG. 7 showing pipeline connections for the urine sampling device 7. A water pipe $Y_1$ is connected to the port 31c and a water pipe $Y_2$ and a mixing pipe $Y_3$ are connected to the water pipe $Y_1$. A solenoid valve $D_1$ equipped with a check valve is provided in the water pipe $Y_2$. The water pipe $Y_2$ is also connected to the flushing cistern 6 for receiving water therefrom. The mixing pipe $Y_3$ is also provided with a solenoid valve $D_3$ having a check valve and has an upper end connected to the nozzle hole 30c of the urine sampling cylinder 30, so that the reagent and diluting water may be supplied through the nozzle member 35 into the urine sampling chamber C.

A water pipe $Y_4$ is connected to the port $31d$ and a water drain pipe $Y_5$ and a reagent pipe $Y_6$ are connected to the water pipe $Y_4$. The water drain pipe $Y_5$ is provided with a solenoid valve $D_2$ having a check valve and is connected to the bowl 8 to discharge water thereinto. The reagent pipe $Y_6$ is also provided with a solenoid valve $D_4$ having a check valve and is connected to the cartridge 21 by the hose 23 for receiving the reagent therefrom.

A water pipe $Y_7$ has one end connected to the spray hole $30d$ of the urine sampling cylinder 30 and is provided with a solenoid valve $D_5$ having a check valve, while the other end of the water pipe $Y_7$ is connected to a pipe of water supply for receiving water therefrom. The washing spray 36 connected to the port $30d$ can spread a jet of water into the urine sampling chamber C.

The thermistor 37 inserted in the thermistor hole $30e$ of the urine sampling cylinder 30 is connected to the control panel 19 by a thermistor cord $37a$ (FIG. 5) for detecting the temperature of the urine sampling chamber C and outputting a corresponding electrical signal to the control panel 19.

Figure 11:
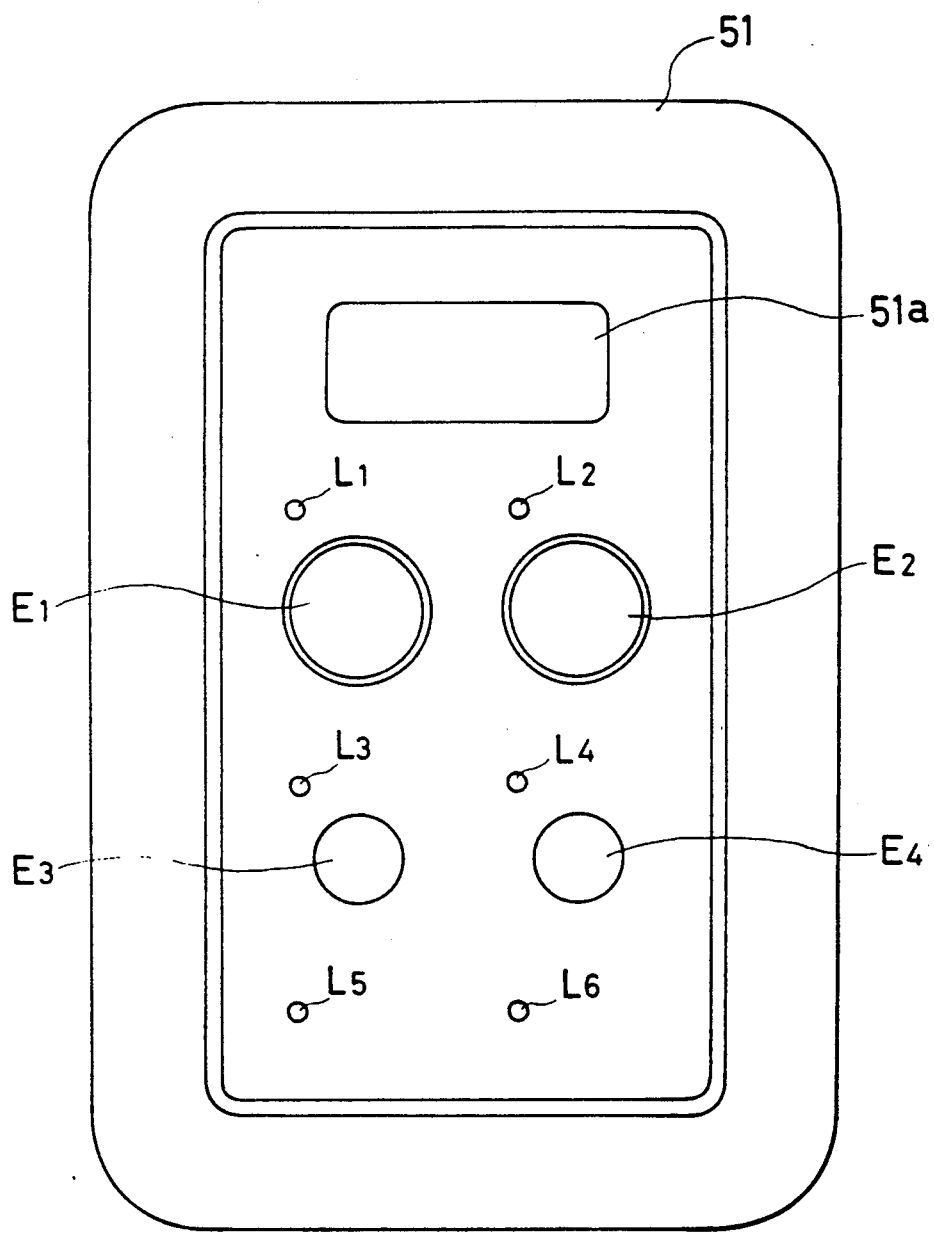
FIG. 11 is a front elevational view of an operating panel.

Referring to FIG. 11, an operating panel 51 is mounted on, for example, the wall of a toilet room in which the toilet stool 1 is installed. The operating panel 51 enables the user of the toilet stool to operate the urine sampling device 7 in accordance with a control program which is established by the control panel 19. The operating panel 51 has near its top a display $51a$ adapted to indicate the concentration of sugar, etc. in the urine numerically. The display $51a$ comprises an LED, etc. A measurement preparing switch $E_1$ and a measurement switch $E_2$ are juxtaposed below the display $51a$. A diluting water supply switch $E_3$ and a reagent supply switch $E_4$ are juxtaposed below the switches $E_1$ and $E_2$. Pilot lamps $L_1$ and $L_2$ are provided between the display $51a$ and the switches $E_1$ and $E_2$, pilot lamps $L_3$ and $L_4$ between the switches $E_1$ and $E_2$ and the switches $E_3$ and $E_4$, and pilot lamps $L_5$ and $L_6$ below the switches $E_3$ and $E_4$.

The cartridge 21 contains an enzymic reagent, or more specifically, glucose oxidase. It is an enzyme which can oxidize glucose in the urine.

Attention is now directed to FIG. 15 which consists of FIGS. $15a$, $15b$ and $15c$ and shows in detail the control which is effected by the control panel 19, while reference is also made to FIGS. 7 and 11. The control panel 19 includes a microcomputer not shown, but containing a read-only memory (ROM) storing the control program shown in FIG. 15.

If an examination start switch is turned on (S1), the proximity switch 28 checks the amount of the reagent in the cartridge 21 (S3) and if it no longer contains any reagent, the lamp $L_6$ on the operating panel 51 (FIG. 11) is lit to indicate the lack of the reagent (S4). On the other hand, the lamp $L_5$ is lit if the cartridge 21 contains a sufficient supply of reagent (S2).

If the preparing switch $E_1$ on the operating panel 51 is pressed by the user (S5), the urine sampling device 7 is placed in operation as will hereinafter be described. If the switch $E_3$ for supplying diluting water is pressed, however, control is effected in accordance with a flow chart shown at D (S51), and if the switch $E_4$ for supplying the reagent is pressed, control is effected in accordance with a flow chart shown at E (S52).

If the preparing switch $E_1$ is pressed, water is supplied from the flushing cistern 6 to the pump chamber P and the urine sampling chamber C and washes the chambers P and C and the pipelines associated therewith, whereby the device 7 is prepared for sampling urine. If the user brings his hand close to the detector 15 of the photoelectric switch 29 on the cistern 6, the photoelectric switch 29 is actuated (S6), whereby the rotary solenoid 14 is turned on to allow flushing water to be supplied from the cistern 6 into the bowl 8 (S7). Simultaneously, the stepping motor 50 is driven for rotation in its normal direction (S8) to raise the table 43 to its uppermost position, i.e. until it abuts on the contact $47a$ of the limit switch 47, whereby the piston 32 is also raised (S10). As soon as the motor 50 starts rotation in its normal direction, the solenoid valve $D_1$ is opened to allow water to flow from the cistern 6 to the pump chamber P through the water pipe $Y_2$ and $Y_1$ (S9). As soon as the limit switch 47 is turned on, the stepping motor 50 starts rotation in its reverse direction to lower the table 43 and the piston 32 to their lowermost positions (S11). The motor 50 is rotated by a predetermined number of revolutions to lower the piston 32 to its lowermost position. This number of revolutions multiplied by the pitch of the screw thread on the screw shaft 45 is equal to the stroke of the piston 32. When the piston 32 is lowered, the solenoid valve $D_1$ is kept closed, but the solenoid valve $D_3$ is opened to allow water to flow from the pump chamber P to the urine sampling chamber C through the water pipe $Y_1$ and the mixing pipe $Y_3$ (S12). After the solenoid valve $D_3$ has been closed, the motor 50 is further rotated in its reverse direction to raise the piston 32 to its uppermost position (S13). The water in the urine sampling chamber C is pushed up by the piston 32 and flows out into the bowl 8. When the piston 32 is raised, the solenoid valve $D_1$ is opened (S14) to allow water to flow from the cistern 6 to the pump chamber P through the water pipe $Y_2$ again. If the solenoid valve $D_1$ is closed, the motor 50 is rotated in its reverse direction again to lower the piston 32 to its lowermost position (S15). As soon as the piston 32 starts to be lowered, the solenoid valve $D_2$ is opened (S16) to allow the water in the pump chamber P to be discharged into the bowl 8 through the water pipe $Y_4$ and the drain pipe $Y_5$. Then, the solenoid valve $D_2$ is closed and the piston 32 is raised again (S17). As soon as the piston 32 starts to be raised, the solenoid valve $D_1$ is opened (S18) to allow water to flow from the cistern 6 to the pump chamber P through the water pipe $Y_2$ again. If the valve $D_1$ is closed, judgment is made in accordance with a signal from the oxygen electrode 34 connected to the urine sampling cylinder 30 to see that the concentration of oxygen in the urine sampling chamber C is at its initial level (S19). In other words, judgment is made to see if the urine sampling chamber C, the pump chamber P, the mixing pipe $Y_3$, the water pipes $Y_1$, $Y_2$ and $Y_4$ and the drain pipe $Y_5$ have been properly washed. If the result of the judgment is YES, the solenoid valve $D_5$, which has been opened at S44, is closed, whereby the supply of water to the urine sampling chamber C through the water pipe $Y_7$ is discontinued (S20) to finish the cleaning of the device. Whenever the preparing switch $E_1$ is pressed (S5), therefore, Steps S6 to S20 ascertain if the urine sampling chamber C, the pump chamber P and the pipelines associated therewith have all been cleaned properly. If they have not been cleaned properly, the sequence of operation is returned from S19 to S11 and S12 and Steps S15 to S18 are repeated.

When the proper cleaning of the device has been ascertained, Step S20 is followed by S21, whereby its operation for urine examination is started. The urine which has been discharged by the user is received in the urine sampling chamber C. The greater part of the urine is removed from the chamber C and water is introduced into the chamber C for diluting the urine remaining therein. When the urine is diluted, the reagent is also introduced into the chamber and the urine, water, and reagent are mixed together. Then, the concentration of oxygen in the chamber is determined by the oxygen electrode 34.

The stepping motor 50 is started to raise the piston 32 (S21). As soon as the motor 50 is started, the solenoid valve $D_1$ (FIG. 7) is opened to allow diluting water to flow from the cistern 6 to the pump chamber P through the water pipes $Y_2$ and $Y_1$ (S22). As soon as the table 43 abuts on the limit switch 47 (S23), the motor 50 is reversed to lower the piston 32 (S24), while the solenoid valve $D_2$ is opened (S25) to allow water to flow from the pump chamber P to the bowl 8 through the drain pipe $Y_5$.

After the solenoid valve $D_2$ is closed, the user seated on the main body 2 of the toilet stool discharges urine into the bowl 8 (S26). The urine is directed toward the third surface portion 8c of the bowl 8 and flows into the urine sampling chamber C having its upper end opening in the third surface portion 8c. As a result of the lowering of the piston 32, the chamber C has an empty space in which the urine is stored.

If the measurement switch $E_2$ on the operating panel 51 is turned on (S27), the stepping motor 50 is rotated to raise the piston 32 (S31). If the switch $E_2$ is not pressed within 10 minutes after the switch $E_1$ has been pressed (S28), the program is shifted to S8'. The stepping motor 50 is started again and is stopped after the urine sampling device 7 has been cleaned (S8' to S20'). Steps S8' to S20' are identical in meaning to S8 to S20, respectively. If the switch $E_1$ is pressed, the lamp $L_1$ is turned on (S29) after flickering at intervals of 0.5 second (S28).

If the switch $E_2$ is pressed in a timely (i.e. within 10 minutes) (S27), the motor 50 is started to raise the piston 32 (S31) and the solenoid valve $D_1$ is opened to allow water to flow from the cistern 6 to the pump chamber P through the pipes $Y_2$ and $Y_1$ After the valve $D_1$ is closed, the motor 50 is reversed to lower the piston 32 (S33) and the solenoid valve $D_3$ is opened (S34), whereby water is supplied from the pump chamber P to the urine sampling chamber C through the pipes $Y_1$ and $Y_3$ and dilutes the urine in the chamber C.

After the valve $D_3$ is closed, the motor 50 is started again to raise the piston 32 (S35), whereby the mixture of urine and water in the urine sampling chamber C is discharged into the bowl 8. Therefore, it is only in the clearance M that the chamber C holds the mixture of urine and water when the piston 32 has been raised to its uppermost position.

When the piston 32 is raised, the solenoid valve $D_4$ is opened to allow the reagent to be drawn from the cartridge 21 to the pump chamber P through the pipes $Y_6$ and $Y_4$ (S35N). After the valve $D_4$ is closed (S35N), the solenoid valve $D_3$ is opened (S37) and the motor 50 is reversed to lower the piston 32 (S36). The reagent is supplied from the pump chamber P to the urine sampling chamber C and is mixed with the urine and water in the chamber C. As the reagent is spread into the chamber C through the nozzle member 35, it is mixed very easily with the urine and water in the chamber C.

The reagent is supplied into the chamber C after the greater part of the urine received in the chamber C has been removed therefrom with the water diluting it (S31 to S37), as hereinabove described. In other words, a small amount of urine is reacted with a large amount of reagent, or is greatly diluted, so that the glucose in the urine can be effectively oxidized by the enzyme. The urine is preferably diluted so that the resulting dilution may have a urine to reagent ratio of, say, 1:30 to 1:50. According to this invention, therefore, it is possible to obtain a very small sample of urine which has hitherto been difficult to obtain in any conventional toilet stool.

Figure 13:
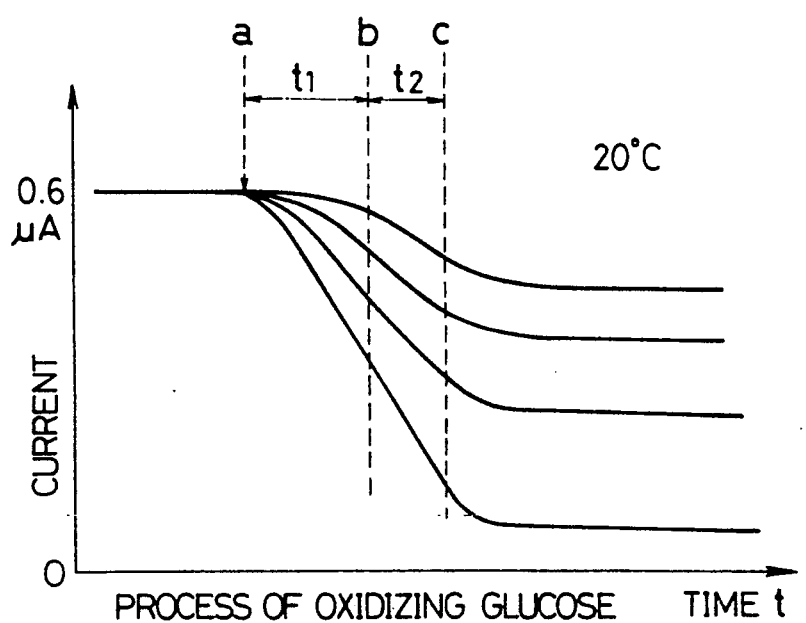
FIG. 13 is a graph showing a variation of electric current in an oxygen electrode in relation to time when a reagent is supplied.

Referring to FIG. 13, point "a" is the point of time at which the reagent, urine and water are mixed in the urine sampling chamber C as a result of Steps S36 and S37. At that point, the glucose in the urine begins to be oxidized by the enzyme and the resulting reduction of oxygen begins to cause an increase of resistance between the poles of the oxygen electrode 34 and thereby a reduction of current flowing thereacross. The oxidation of the glucose is allowed to proceed for a first period of time $t_1$ of, say, 20 seconds between points "a" and "b", and thereafter, the current of the electrode 34 is measured over a second period of time $t_2$ of, say, 10 seconds between points "b" and "c" (S39).

As long as the urine contains a large amount of glucose, oxygen is consumed by the enzyme so rapidly that the electrode 34 shows a sharp reduction of current, but as the amount of glucose decreases, only a smaller reduction of current occurs, as is obvious from FIG. 13. Therefore, it is possible to determine the concentration of sugar in the urine by measuring the variation of current which the oxygen electrode 34 shows. The result of the measurement is inputted to a central processing unit (CPU) in the control panel 19. At the same time, the temperature of the urine sampling chamber C is measured by the thermistor 37 (S38) and is inputted to the CPU, too. If the temperature i low, the reaction between the glucose in the urine and the enzymic reagent is not active, as is obvious from FIG. 14 showing graphically the relationship between the reaction rate and the concentration of glucose at different temperatures.

Figure 14:
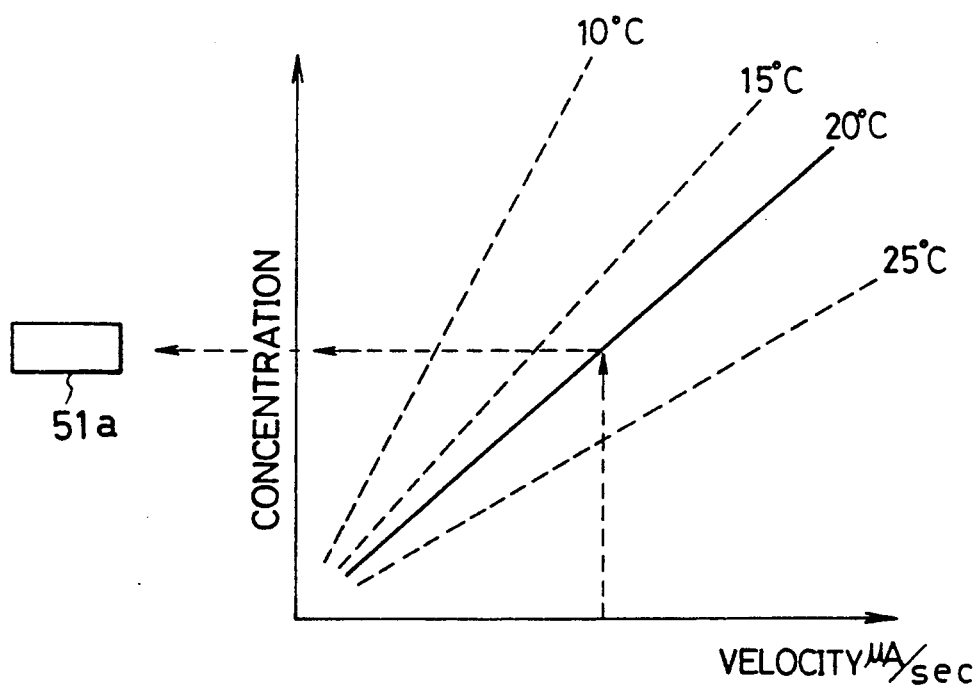
FIG. 14 is a graph showing the relation between the variation of electric current per unit time and the concentration of glucose.
Figure 15A:
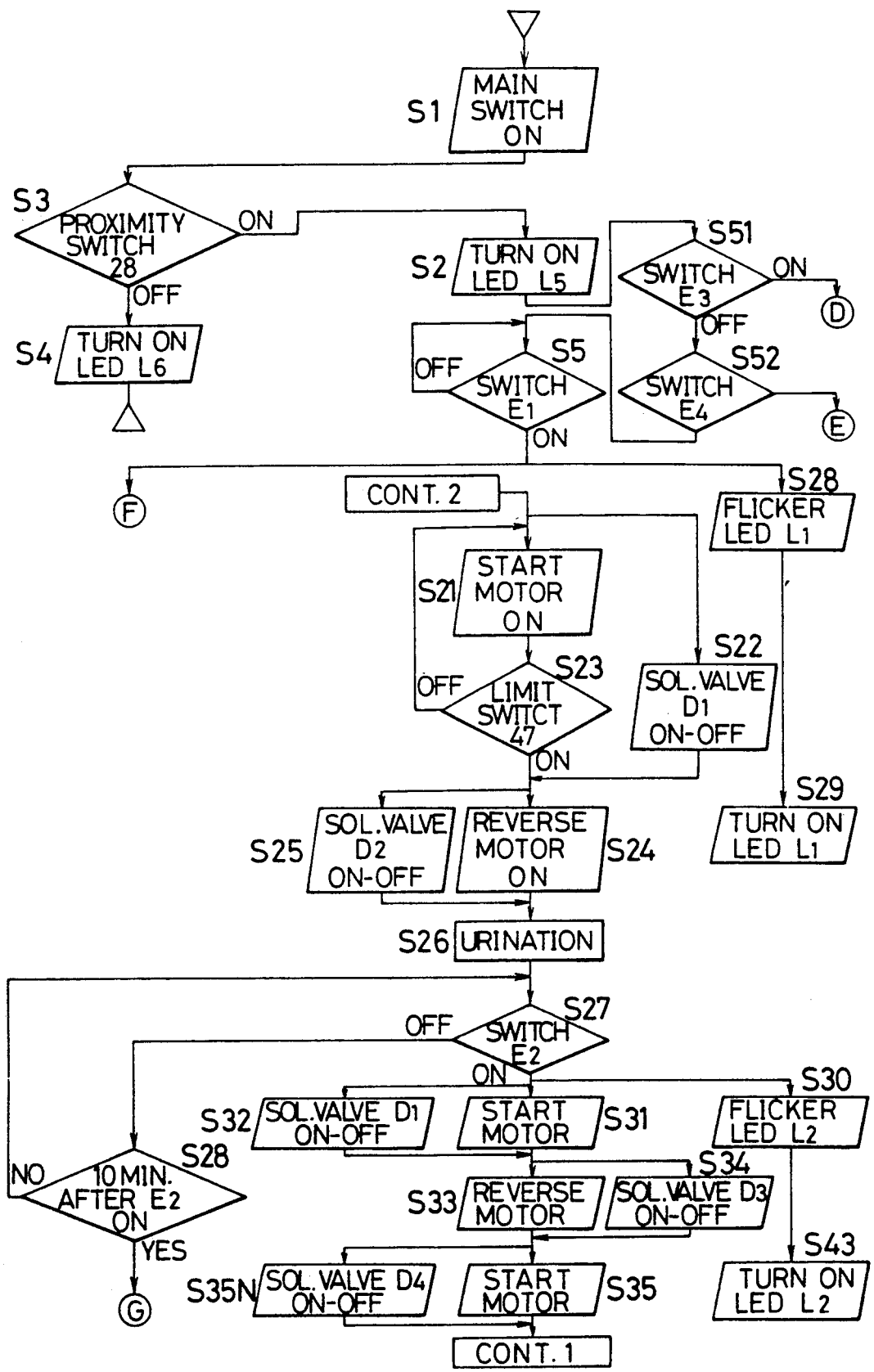
Figure 15B:
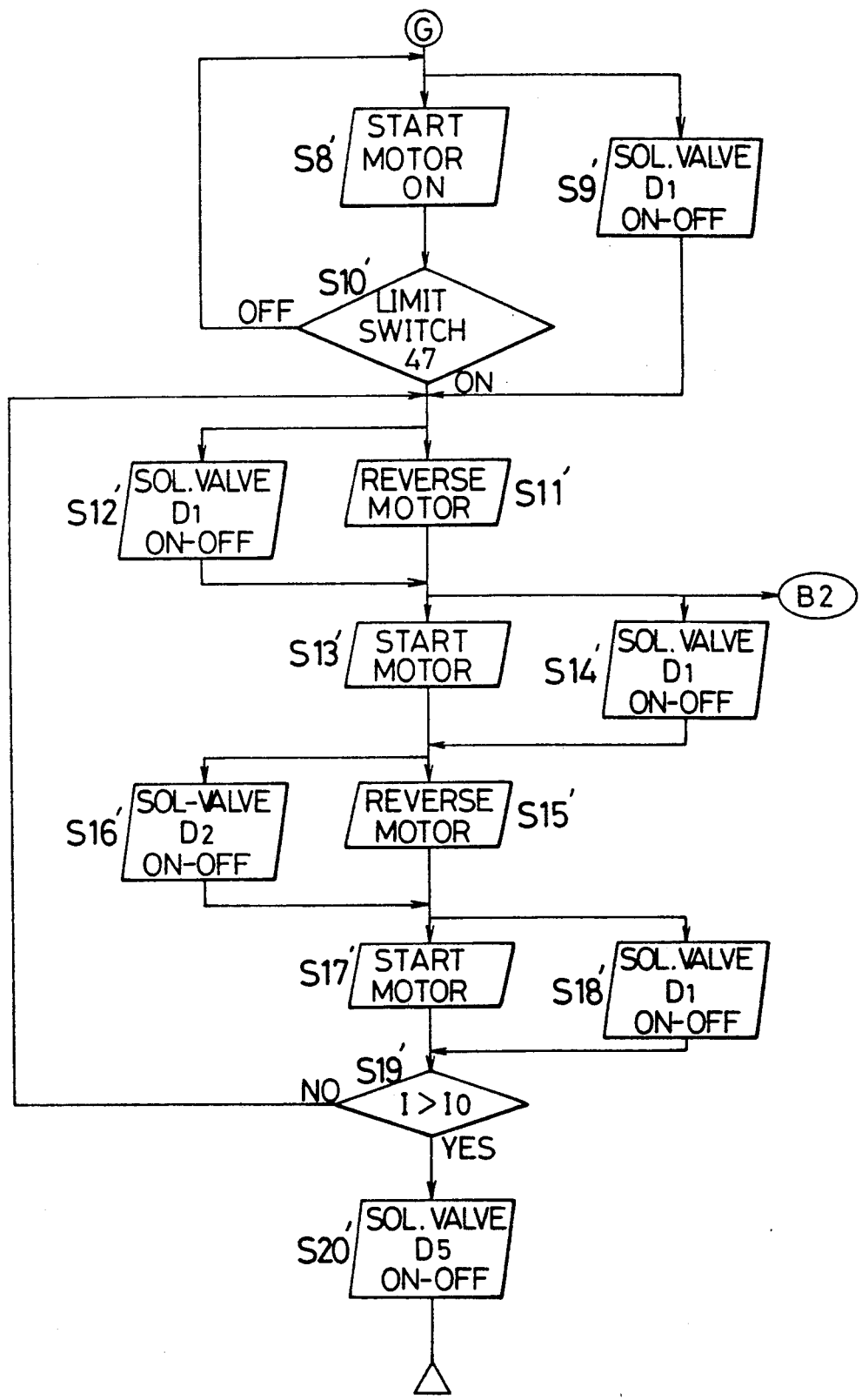
Figure 15D:
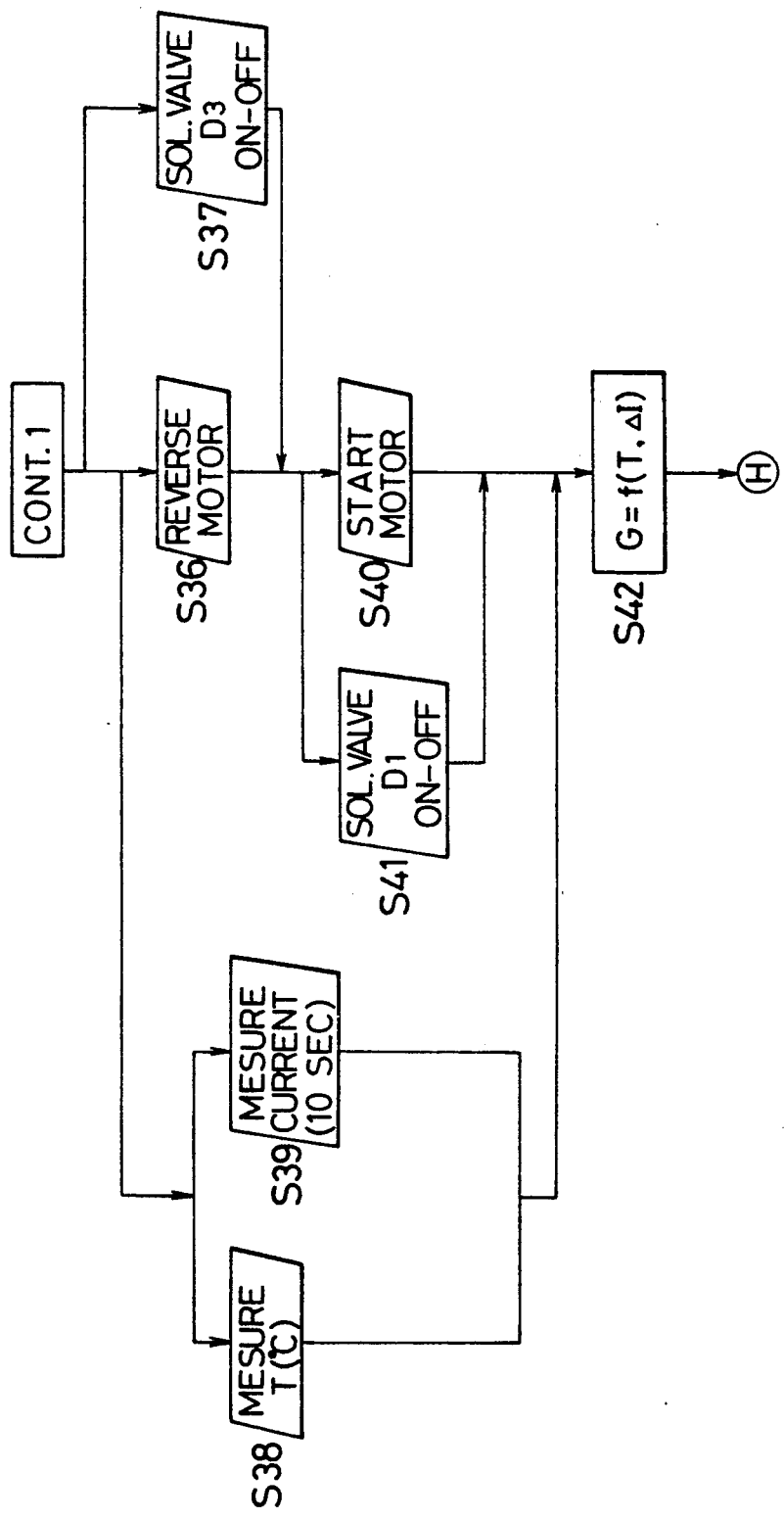
Figure 15F:
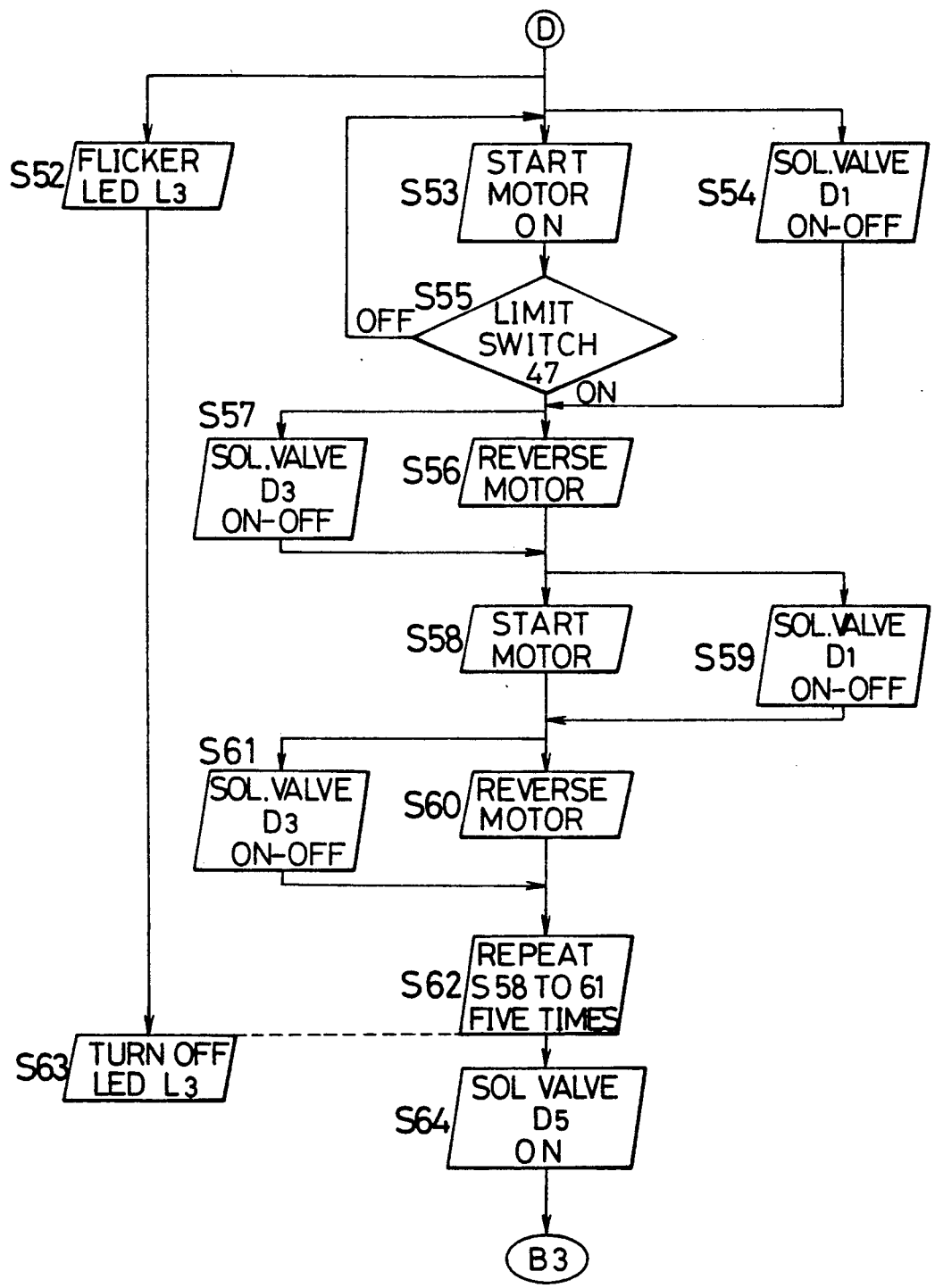
Figure 16:
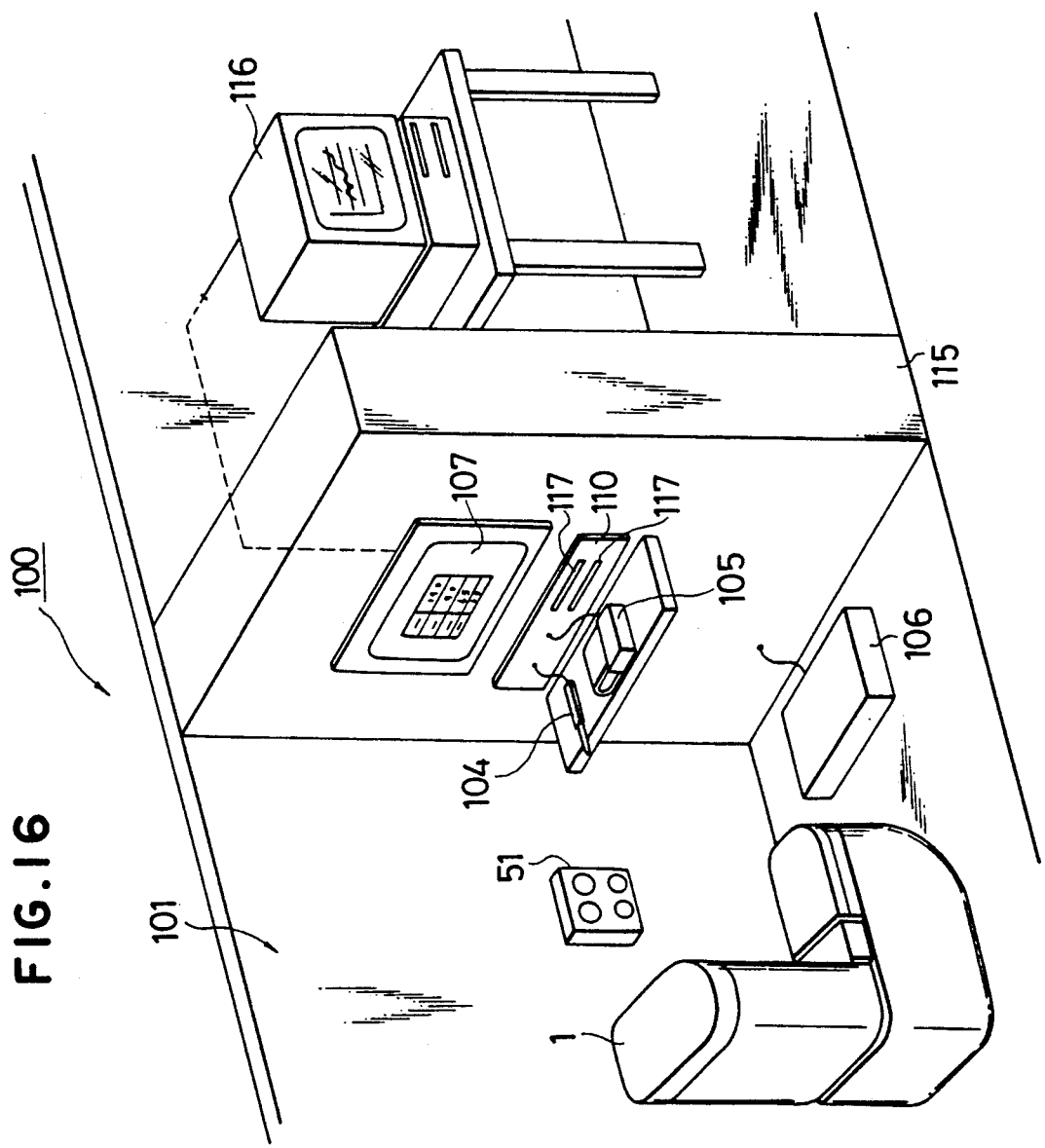
FIG. 16 is a perspective view of a system for collecting information on health.

The curves shown in FIG. 14 represent data obtained from the measurement of current over the period of 10 seconds between points "b" and "c" in FIG. 13 (S39) and stored in the ROM. The axis of abscissa in FIG. 14 represents the rate obtained from the measurement of current between points "b" and "c" (variation of current over the period of 10 seconds, A/T), while the axis of ordinate shows the concentration of glucose in the urine. It is possible to find the concentration of glucose instantaneously from the rate inputted as a result of Step S39. The concentration of glucose corresponding to the temperature which has been inputted through the thermistor 37 (S38) is calculated in the CPU from the curves of FIG. 14 (S42). The concentration is numerically shown on the display 51a of the operating panel 51 (S48).

An electronic buzzer sounds to indicate the completion of the measurement (S47). After the display has shown the result for a predetermined length of time, the lamp $L_2$ is turned off (S49) and the lamp $L_1$ is also turned off (S50).

After the display 51a has shown the concentration of glucose for a predetermined number of seconds, the urine sampling device 7 is flushed with a large amount of water. The stepping motor 50 is started to raise the piston 32 (S40), whereby the mixture of reagent, urine and water in the urine sampling chamber C is discharged into the bowl 8. The solenoid valve $D_1$ is opened to introduce water from the cistern 6 to the pump chamber P through the pipes $Y_2$ and $Y_1$ (S41).

Then, the solenoid valve $D_5$ is opened to introduce water into the urine sampling chamber C through the pipe $Y_7$ to wash the chamber C (S44). The motor 50 is rotated to lower the piston 32 (S45) and the solenoid valve $D_3$ is opened (S46) to allow water to flow from the pump chamber P to the urine sampling chamber C, whereby the pipes $Y_1$ and $Y_3$ are washed.

After the valve $D_3$ has been closed, the motor 50 is rotated again to raise the piston 32 (S13″) and the valve $D_1$ is opened (S14″) to allow water to flow from the cistern 6 to the pump chamber P, whereby the pipe $Y_1$ is washed again. The motor 50 is reversed to lower the piston 32 (S15″) and the solenoid valve $D_2$ is opened (S16″), whereby water is discharged from the pump chamber P to wash the pipes $Y_4$ and $Y_5$ Steps S17″ to S20″ are thereafter followed to effect the satisfactory cleaning of the pipelines, whereby the self-cleaning operation of the urine sampling device 7 is completed. Steps S13″ to S20″ are identical in meaning to S13 to S20, respectively.

As a result of the vertical movement of the piston 32, therefore, water is introduced into the pump chamber P and is, then, supplied to the urine sampling chamber C to dilute the urine which has been collected therein. As the piston 32 is raised, the diluted urine is discharged from the chamber C until only a small amount of diluted urine remains in the clearance M. As the piston 32 is lowered, the reagent which has been drawn into the pump chamber P is caused to jet into the urine sampling chamber C and is mixed with the urine in the chamber C. As a large amount of reagent is mixed with a small amount of urine, the reagent can effectively oxidize the glucose in the urine, and the concentration of the glucose can be displayed numerically. Then, the vertical movement of the piston 32 causes the chambers C and P and the pipelines associated therewith to be flushed with water, so that the urine sampling device may be ready for a new cycle of operation.

If after Step S2, the button $E_3$ for supplying diluting water is pressed (S51), the lamp $L_3$ is caused to flicker (S52) and the operation of the device is carried out in accordance with the program shown at D. The stepping motor 50 is started (S53) to raise the piston 32 until the table 43 abuts on the limit switch 47 (S55), and the solenoid valve $D_1$ is opened (S54) to allow water to flow from the cistern 6 to the pump chamber P. The motor 50 is reversed to lower the piston 32 (S56) and the solenoid valve $D_3$ is opened (S57) to allow water to flow from the pump chamber P to the urine sampling chamber C. The motor 50 is rotated again to raise the piston 32 (S58) and the solenoid valve $D_1$ is opened to allow water to flow into the pump chamber P again (S59). The motor 50 is reversed to lower the piston 32 (S60) and the valve $D_3$ is opened to allow water to flow from the pump chamber P to the urine sampling chamber C (S61). Steps S58 to S61 are repeated five times for removing bubbles from the pipes.

The removal of bubbles from the pipes is carried out, for example, immediately after installation of the urine sampling device 7 to prevent bubbles from exerting any undesirable effect on the degree of dilution of urine or the mixing ratio of the reagent and thereby ensure that correct results of measurement be obtained. Finally, the valve $D_5$ is opened to introduce water into the urine sampling chamber C (S64), whereafter Steps S13 to S20 are carried out in accordance with the program shown at B.

If the switch $E_4$ for supplying the reagent is pressed, the program shown at E is carried out. This is the operation which occurs when the cartridge 21 is changed. If the switch $E_4$ is pressed (S65), the lamp $L_4$ flickers (S66) and the motor 50 is started to raise the piston 32 (S67). The solenoid valve $D_4$ is opened (S68) to allow the reagent to be drawn into the pump chamber P. If the limit switch 47 is turned on (S69), the motor 50 is reversed to lower the piston 32 (S70) and the valve $D_3$ is opened (S71) to allow the reagent to flow from the pump chamber P to the urine sampling chamber C. The motor 50 is started again to raise the piston 32 (S72) and the valve $D_4$ is opened (S73) to introduce the reagent into the pump chamber P again. The motor 50 is reversed again to lower the piston 32 (S74) and the valve $D_3$ is opened (S75) to allow the reagent to flow from the pump chamber P to the urine sampling chamber C. Steps S72 to S75 are repeated five times to remove bubbles from the reagent pipe $Y_6$ and the water pipe $Y_4$. Finally, the valve $D_5$ is opened (S77) to introduce water into the chamber C and thereby purge the reagent, whereupon the lamp $L_4$ is turned off (S78).

Although the cartridge 21 has been described as containing glucose oxidase, it can alternatively contain bilirubin oxidase, so that the device may be able to determine the concentration of bilirubin in the urine and thereby be useful for the diagnosis of a disease of the liver. If the cartridge 21 contains a reagent consisting mainly of lactate dehydrogenase, the device can effectively determine the concentration of lactic acid in the urine. If it contains cholesterol oxidase, the device can easily determine the concentration of oils and fats in the urine. The cartridge 21 may contain only a single reagent, or a mixture of two or more reagents. Even if no cartridge of the type containing a mixture of reagents, it is possible to obtain a toilet stool which can examine urine for not only sugar, but also bilirubin, lactate and oils and fats, if it is provided with an appropriate number of separate urine sampling devices 7 and cartridges 21.

The urine sampling device 7 includes the piston which is vertically movable to thereby change alternately the volumes of the lower pump chamber and the upper urine sampling chamber, so that the diluting water and the reagent may be effectively supplied into the chambers, while the reagent which is supplied into the urine sampling chamber through the nozzle member 35 is effectively mixed with the urine in the urine sampling chamber and reacted therewith. Moreover, only a small amount of urine remaining in the clearance M is used as a sample of urine which is reacted with a large amount of reagent, so that it is possible to examine the urine for glucose, etc. very accurately.

The rotary solenoid 14 is installed in the cistern 6. It requires only a small space for installation and operation, as compared with a vertically slidable solenoid, and the cistern 6 can, therefore, store a sufficiently large amount of water. The rotary solenoid has also the advantage of not making any substantial noise when it is operated. As the photoelectric switch 29 for operating the rotary solenoid 14 is of the type including optical fibers, it has no portion projecting into the cistern 6, but the detector 15 can be snugly fitted in the wall of the cistern. As the fibers do not require any electrical wiring, they can be laid in the water in the cistern and the photoelectric switch can maintain a good operating condition without having any electrical fault otherwise caused by the water in the cistern.

Figure 17:
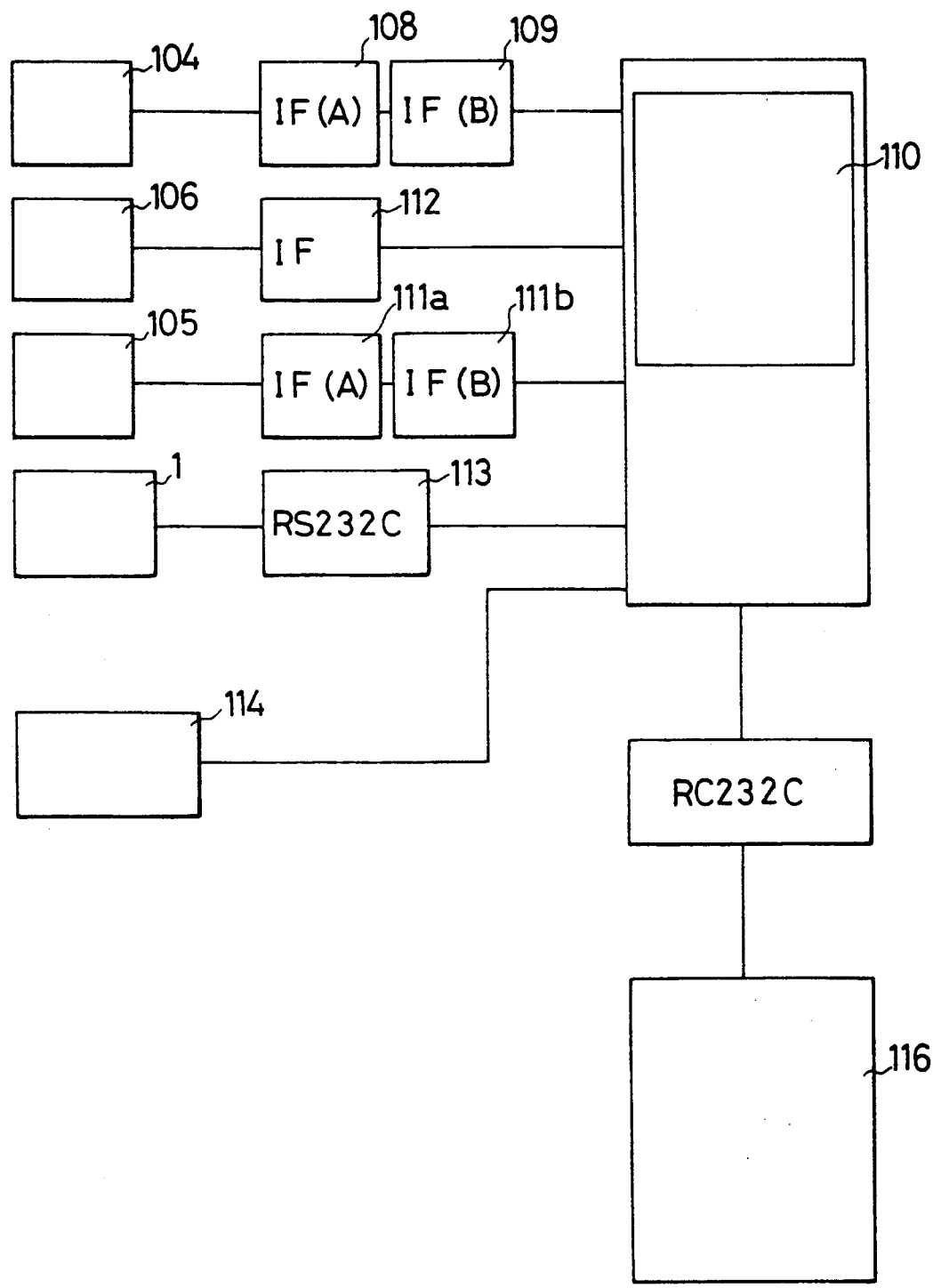
FIG. 17 is a block diagram showing an interface between a thermometer, a scale, a sphygmomanometer, a toilet stool and a touch screen, and an operating personal computer and a data transmitting personal computer.
Figure 18:
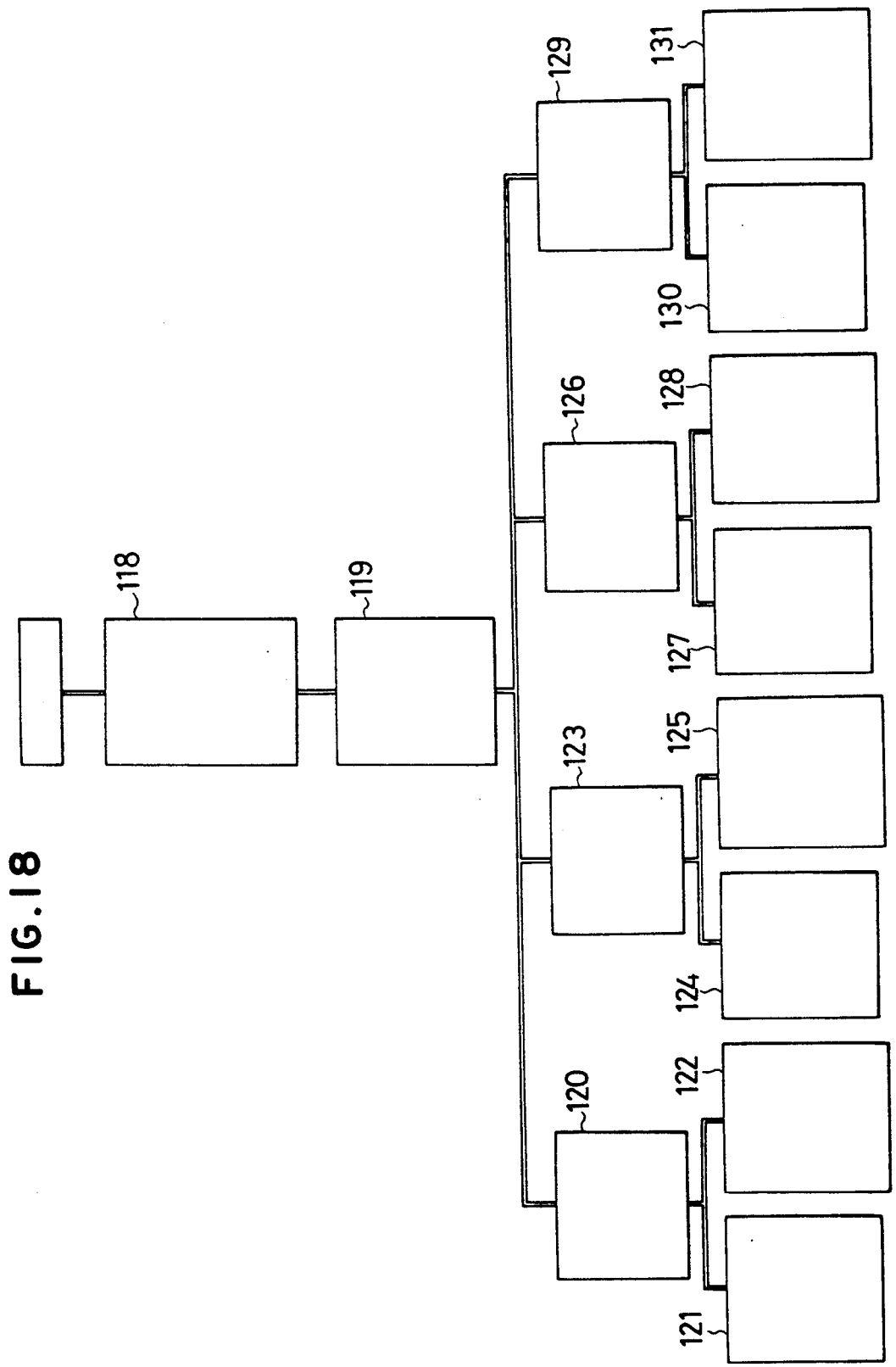
FIG. 18 is a block diagram showing a variety of pictures displayed on a CRT.

The operating panel 51 and the control panel 19 are connected to an operating personal computer 110 through RS232C as shown at 113 in FIG. 17, so that the results of measurements, such as the concentration of sugar, may be inputted to the computer 110.

A system for collecting information on health will now be described with reference to FIGS. 16 to 19. It includes the toilet stool which has hereinabove been described. The system is generally shown at 100 in FIG. 16. The toilet stool 1, the operating panel 51, a thermometer 104, a sphygmomanometer 105, a scale 106 and a CRT 107 are installed in a toilet room 101.

The thermometer 104 is an ordinary electronic thermometer which can measure the temperature of a person using it based on its rise per unit time. The temperature as measured and expressed by an analog value is converted to a digital one by interfaces 108 and 109 and inputted to the computer 110, as shown in FIG. 17.

The sphygmomanometer 105 is an ordinary automatic type instrument into which air is automatically supplied as soon as the measurement of blood pressure is started. The data as obtained by the sphygmomanometer 105 are inputted to the computer 110 through interfaces 111a and 111b.

The scale 106 is of the digital type and is installed in front of the toilet stool 1. The data as obtained by the scale 106 are inputted to the computer 110 through an interface 112.

The computer 110 is of the 16-bit type and is mounted on the wall 115 of the toilet room 101. The CRT 107 is installed on the wall 115 above the computer 110. The CRT 107 has a transparent touch screen 114 which can be pressed for operating the computer 110. The computer 110 is provided with two floppy disk drives 117.

The computer 110 is connected to a personal computer 116 installed in the hospital of a home doctor by communication lines including RC232C. The data on the temperature, weight and blood pressure and the results of urine examination are collected by the computer 110 in the toilet room and are automatically transferred to the computer 116 in the hospital for storage in floppy disks, or other memory devices. If one measures his temperature, weight and blood pressure and examines his urine in the toilet room 101 every day, the results are recorded in the computer 116 in his home doctor's hospital as information on his health.

In operation, a floppy disk is inserted in the disk drive 117 on the computer 110 and a power source switch is turned on. A program is read from the floppy disk and an ID mode picture is displayed on the CRT 107 as shown at 118 in FIG. 18. As the picture 118 shows all the members of a family, the user has to press that portion of the picture which shows him or her. An examination menu 119 appears on the screen to enable the user to choose any item of examination from temperature, weight, blood pressure and urine.

If he chooses temperature, a menu 120 appears on the CRT 107 to enable him to choose either measurement or display. If he chooses display, data on his temperature as obtained, for example, during the past 30 days are displayed graphically on the screen.

If he chooses measurement from the menu 120, operating guidelines 121 appear on the screen and include the following directions:

"1. Put the sensor in the armpit;

2. Do not move until the result of measurement appears."

The result of measurement (i.e. temperature) is eventually displayed on the screen. Then, he is required to choose display, examination, or termination. If he chooses display, the graphic representation 122 of his data appears on the screen. If he chooses examination, the examination menu 119 appears again. If he chooses termination, his examination is terminated and the results of examination are displayed as shown at 132 in FIG. 19. He is, however, required to choose examination on the screen 121 to have all of the four items, i.e. temperature, weight, blood pressure and urine, measured or examined.

If he chooses examination, the examination menu 119 appears on the screen. As he has already measured his temperature, he chooses weight now. A menu 123 appears on the screen and requires him to choose either measurement or display. If he chooses display, data on his weight as obtained, for example, during the past 30 days are displayed on the screen as shown at 125.

If he chooses measurement from the menu 123, operating guidelines 124 appear on the screen and include the following directions:

"1. Ride on the scale calmly;

2. Do not move until the result of measurement appears."

The result of measurement (i.e. weight) is eventually displayed on the screen. Then, he is required to choose display, examination or termination. He chooses examination, insofar as he has not finished all of the four items as yet.

If he chooses examination, the examination menu 119 appears again on the screen. As he has already finished the measurement of his temperature and weight, he chooses blood pressure. A menu 126 appears on the screen and requires him to choose measurement or display. If he chooses display, data on his blood pressure as obtained, for example, during the past 30 days are graphically displayed on the screen as shown at 128.

If he chooses measurement from the menu 126, operating guidelines 127 appear on the screen and include the following directions:

"1. Put the arm band about your arm;

2. Do not move until the result of measurement appears."

The result of measurement (i.e. blood pressure) is eventually displayed on the screen. Then, he is required to choose display, examination or termination and chooses examination.

If he chooses examination, the examination menu 119 appears again. He chooses urine, as he has not yet finished his urine examination. A menu 129 appears on the screen and requires him to choose measurement or display. If he chooses display, data on his urine as obtained, for example, during the past 30 days are graphically displayed on the screen as shown at 131.

If he chooses measurement from the menu 129, operating guidelines 130 appear on the screen. In accordance with the directions appearing on the screen, he operates the operating panel 51 for the urine sampling device so that his urine may be examined for glucose, etc. The result of examination (i.e. concentration of sugar, etc.) is displayed on the screen, as well as on the panel 51. He is required to choose display, examination or termination and can now choose termination, as he has finished all of the four items.

Figure 19:
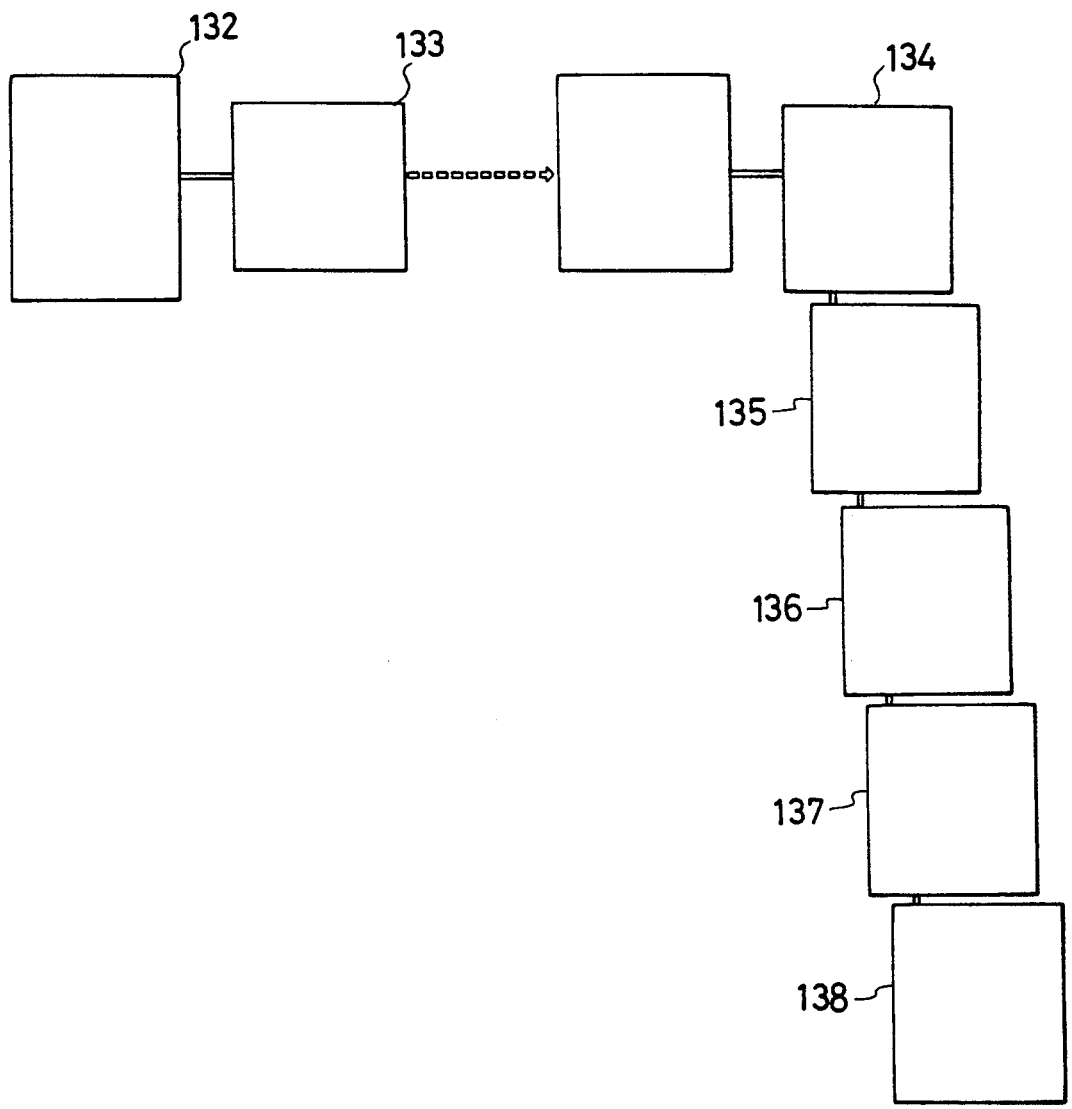
FIG. 19 is a block diagram showing a picture indicating the results of measurements and a picture displayed on a home doctor's personal computer and indicating transmitted data.

If he chooses termination, the picture 132 appears as shown in FIG. 19. It displays the results of the four items of examination and also requires him to choose YES or NO with respect to the transfer of data. If he chooses YES, a picture 133 showing that the data are being transferred, and the data are transferred to the computer 116 in the hospital of his home doctor through the communication line. The data which have been transferred are classified into temperature, weight, blood pressure and urine and are automatically recorded in E files 134 to 137, respectively. The files 134 to 137 are automatically renewed whenever new data have been transferred, so that information on his health may be stored every day in his home doctor's hospital. The doctor may review the information every day or at other regular intervals of time and record his findings in a file 138 in the form of a clinical chart. If he finds anything abnormal, he may communicate with the person who has transmitted the relevant data, and advise him to consult him for a further medical examination.

The system of this invention enables anybody to receive consultation of a doctor at his own home without going to the hospital only if he transfers information on his health to the doctor. On the other hand, the doctor can examine a large number of people within a short time, as he need not receive them in his consultation room, but usually has only to review the information which he has received from them through the system of this invention.

What is claimed is:

1. A system for collecting information on health, comprising,
   a first computer having operating means for operating the computer according to a program,
   health examination means for measuring physical condition of a patient to be examined, said health examination means being connected to the first computer so that information of the patient measured by the health examination means is recorded in the first computer, said health examination means including means for examining contents of urine, means for measuring temperature, means for measuring weight and means for measuring blood pressure, said means for examining contents of urine including a toilet stool; vertical disposed cylinder means having a tits upper end an opening defining an inlet for urine, said opening being located int he toilet stool, said cylinder means including a wall portion, and an enlarged space having a diameter which is larger than that of a remaining portion; piston means provided vertically movably in said cylinder means; means for moving said piston means vertically in said cylinder means; an electrode extending through the wall portion near the enlarged space of said cylinder means and having an end adapted to contact with a liquid in said cylinder means for detecting a constituent of said liquid; reagent supply means including a cartridge, a pipeline, a valve situated in the pipeline, and a pump, said cartridge being connected to the space of the cylinder means through the pipeline, valve nd pump so that a reagent may be supplied into said cylinder means when said valve is opened; and water supply means including a source of water supply, a pipeline connected to the space inside said wall portion and a valve provided in said pipeline of the water supply means, so that water may be supplied into said cylinder means when said valve of the water supply means is opened, and
   a second computer located away from the first computer and electrically connected to the first computer, said second computer storing data transferred from the first computer so that the stored data in the second computer can be examined at desired location and time.

2. A system according to claim 1, wherein said first computer is located in a place where there is no doctor, and the second computer is located in a place where there is a doctor so that the doctor can examine physical condition of the patient away from the patient.

3. A system according to claim 1, wherein said operating means includes a CRT, one menu of said means for examining contents of urine, said means for measuring temperature, said means for measuring weight and said means for measuring blood pressure being displayed on the CRT so that the desired health examination means is selected and physical condition thus selected is measured.

4. A system according to claim 3, wherein said CRT includes a touch screen, which can be pressed for operating the computer.

* * * * *